United States Patent
Irimia et al.

(10) Patent No.: US 11,460,465 B2
(45) Date of Patent: Oct. 4, 2022

(54) CELL CHEMOTAXIS ASSAYS

(71) Applicant: The General Hospital Corporation, Boston, MA (US)

(72) Inventors: Daniel Irimia, Charlestown, MA (US); Caroline Jones, Charlestown, MA (US); Anh Hoang, Brighton, MA (US)

(73) Assignee: The General Hospital Corporation, Boston, MA (US)

( * ) Notice: Subject to any disclaimer, the term of this patent is extended or adjusted under 35 U.S.C. 154(b) by 209 days.

(21) Appl. No.: 16/885,760

(22) Filed: May 28, 2020

(65) Prior Publication Data

US 2020/0292528 A1 Sep. 17, 2020

Related U.S. Application Data

(62) Division of application No. 15/023,588, filed as application No. PCT/US2014/056614 on Sep. 19, 2014, now Pat. No. 10,670,583.

(Continued)

(51) Int. Cl.
*G01N 33/50* (2006.01)
*G01N 15/14* (2006.01)
(Continued)

(52) U.S. Cl.
CPC ........ *G01N 33/5029* (2013.01); *B01L 3/5027* (2013.01); *C12M 27/20* (2013.01);
(Continued)

(58) Field of Classification Search
CPC ..... B01L 2200/0668; B01L 2300/0803; B01L 2300/0867; B01L 2400/0472;
(Continued)

(56) References Cited

U.S. PATENT DOCUMENTS 5,744,366 A 4/1998 Kricka et al.
6,238,874 B1 5/2001 Jarnagin et al.
(Continued)

FOREIGN PATENT DOCUMENTS

WO WO 02/44730 6/2002
WO WO 2009/102453 8/2009
(Continued)

OTHER PUBLICATIONS

Muinonen-Martin AJ, Veltman DM, Kalna G, Insall RH. An improved chamber for direct visualisation of chemotaxis. PLoS One. 2010;5(12):e15309. Published Dec. 14, 2010. doi:10.1371/journal.pone.0015309 (Year: 2010).*

(Continued)

*Primary Examiner* — Jennifer Wecker
*Assistant Examiner* — Jonathan Bortoli
(74) *Attorney, Agent, or Firm* — Fish & Richardson P.C.

(57) ABSTRACT

A device includes an input chamber, an attractant chamber, a migration channel arranged in fluid communication between an outlet of the input chamber and inlet of the attractant chamber, a baffle arranged in fluid communication between the outlet of the input chamber and the migration channel or within the migration channel, and an exit channel in fluid communication with the migration channel at a point beyond the baffle and before the migration channel enters the inlet of the attractant chamber. The baffle is configured to inhibit movement of a first type of cell through the baffle to a greater extent than the baffle inhibits movement of a second type of cell through the baffle.

18 Claims, 13 Drawing Sheets

Related U.S. Application Data

(60) Provisional application No. 61/880,591, filed on Sep. 20, 2013.

(51) Int. Cl.
*B01L 3/00* (2006.01)
*C12M 1/00* (2006.01)
*G01N 15/10* (2006.01)
*G01N 15/00* (2006.01)

(52) U.S. Cl.
CPC ..... *G01N 15/1463* (2013.01); *G01N 15/1484* (2013.01); *G01N 33/5047* (2013.01); *B01L 2200/0668* (2013.01); *B01L 2300/0803* (2013.01); *B01L 2300/0867* (2013.01); *B01L 2400/0472* (2013.01); *B01L 2400/086* (2013.01); *G01N 2015/0065* (2013.01); *G01N 2015/1006* (2013.01); *G01N 2015/1075* (2013.01); *G01N 2015/1486* (2013.01)

(58) Field of Classification Search
CPC . B01L 2400/086; B01L 3/5027; C12M 27/20; G01N 15/1463; G01N 15/1484; G01N 2015/0065; G01N 2015/1006; G01N 2015/1075; G01N 2015/1486; G01N 33/5029; G01N 33/5047
See application file for complete search history.

(56) References Cited

U.S. PATENT DOCUMENTS

| | | | |
|---|---|---|---|
| 6,921,660 | B2 | 7/2005 | Kirk et al. |
| 7,326,563 | B2 | 2/2008 | Enoch et al. |
| 7,374,906 | B2 | 5/2008 | Kirk et al. |
| 8,921,122 | B2 | 12/2014 | Irimia |
| 10,625,258 | B2* | 4/2020 | Desmond ............. C12Q 1/6844 |
| 2002/0168757 | A1 | 11/2002 | Kirk et al. |
| 2005/0271548 | A1 | 12/2005 | Yang et al. |
| 2007/0264675 | A1 | 11/2007 | Toner et al. |
| 2011/0117579 | A1 | 5/2011 | Irimia |
| 2011/0124025 | A1 | 5/2011 | Castrocane et al. |
| 2012/0094325 | A1 | 4/2012 | Irimia |
| 2012/0216601 | A1 | 8/2012 | Irimia |
| 2012/0315660 | A1 | 12/2012 | Schroeder et al. |
| 2013/0244270 | A1 | 9/2013 | Xie et al. |

FOREIGN PATENT DOCUMENTS

| | | |
|---|---|---|
| WO | WO 2010/036913 | 4/2010 |
| WO | WO 2010/108095 | 9/2010 |
| WO | WO 2015/042436 | 3/2015 |

OTHER PUBLICATIONS

Englert DL, Manson MD, Jayaraman A. Flow-based microfluidic device for quantifying bacterial chemotaxis in stable, competing gradients. Appl Environ Microbiol. 2009;75(13):4557-4564. doi:10.1128/AEM.02952-08 (Year: 2009).*

Agrawal et al., "Neutrophil migration assay from a drop of blood," Lab Chip., 8(12):2054-2061, Epub Oct. 30, 2008.

Albini and Benelli "The chemoinvasion assay: a method to assess tumor and endothelial cell invasion and its modulation" Nat Protoc. 2(3):504-511 (2007).

Beningo et al. "Responses of fibroblasts to anchorage of dorsal extracellular matrix receptors" Proc Natl Acad Sci USA 101(52):18024-18029 (2004).

Bovin and Gabius "Polymer-immobilized carbohydrate ligands: Versatile Chemical Tools for Biochemistry and Medical Sciences" Chemical Society Reviews 24(6):413-421 (1995).

Boyden "The Chemotactic Effect of Mixtures of Antibody and Antigen on Polymorphonuclear Leucocytes" Journal of Experimental Medicine 115 (3):453-466 (1962).

Brandley and Schnaar "Cell-Surface Carbohydrates In Cell Recognition And Response" Journal of Leukocyte Biology 40:97-111 (1986).

Buffone et al., "Neutrophil function in surgical patients. Relationship to adequate bacterial defenses," Arch Surg., 119(1):39-43, Jan. 1984.

Butler et al., "Burn injury reduces neutrophil directional migration speed in microfluidic devices," PLoS One., 5(7):e11921, 12 pages, Jul. 30, 2010.

Carmignani et al. "Intraperitoneal cancer dissemination: Mechanisms of the patterns of spread" Cancer Metastasis Rev. 22:465-472 (2003).

Cavallaro and Christofori "Cell adhesion and signalling by cadherins and Ig-CAMs in cancer" Nature Reviews Cancer 4:118-132 (2004).

Chiang and Massague "Molecular Basis of Metastasis" N Engl J Med. 359 (26):2814-2823 (2008).

Condeelis and Segall "Intravital imaging of cell movement in tumours" Nature Reviews Cancer 3:921-930 (2003).

Decaestecker et al. "Can anti-migratory drags be screened in vitro? A review of 2D and 3D assays for the quantitative analysis of cell migration" Medicinal Research Reviews 27(2):149-176 (2007).

Demou and McIntire "Fully automated three-dimensional tracking of cancer cells in collagen gels: Determination of motility phenotypes at the cellular level" Cancer Research 62(18):5301-5307 (2002).

Even-Ram and Yamada "Cell migration in 3D matrix" Current Opinion in Cell Biology 17:524-532 (2005).

Feki et al. "Dissemination of intraperitoneal ovarian cancer: Discussion of mechanisms and demonstration of lymphatic spreading in ovarian cancer model" Crit Rev Oncol Hematol. 72:1-9 (2009).

Friedl and Wolf "Tumour-cell invasion and migration: Diversity and escape mechanisms" Nature Reviews Cancer 3:362-374 (2003).

Gerhardt and Semb "Pericytes: gatekeepers in tumour cell metastasis?" J Mol Med 86:135-144 (2008).

Giese and Westphal "Glioma invasion in the central nervous system" Neurosurgery 39(2):235-252 (1996).

Hamza and Irimia, "Whole blood human neutrophil trafficking in a microfluidic model of infection and inflammation," Lab on a Chip, May 2015, 15: 2625-2633.

Hanahan and Weinberg "The Hallmarks of Cancer" Cell 100:57-70 (2000).

Hansson et al., "Inflammation and atherosclerosis," Annu Rev Pathol., 1:297-329, 2006.

Hasenberg et al., "Rapid immunomagnetic negative enrichment of neutrophil granulocytes from murine bone marrow for functional studies in vitro and in vivo," PLoS One, 6(2):e17314, 11 pages, Feb. 23, 2011.

Hoang et al., "Measuring neutrophil speed and directionality during chemotaxis, directly from a droplet of whole blood," Technology, Oct. 2013, 1: 49-57.

International Preliminary Report on Patentability dated Sep. 29, 2011 issued in International application No. PCT/US2010/027980, 6 pages.

International Preliminary Report on Patentability for PCT/US2014/056614, dated Mar. 31, 2016, 8 pages.

International Preliminary Report on Patentability in International Application No. PCT/US2017/031557, dated Nov. 15, 2018, 8 pages.

International Search Report and Written Opinion dated Oct. 26, 2010 issued in International application No. PCT/US2010/027980, 14 pages.

International Search Report and Written Opinion dated Sep. 28, 2009 from International application No. PCT/US2009/000890, 15 pages.

International Search Report and Written Opinion for PCT/US2014/056614, dated Dec. 30, 2014, 14 pages.

International Search Report and Written Opinion in International Application No. PCT/US2017/031557, dated Sep. 22, 2017, 16 pages.

Irimia et al. "Adaptive-Control Model for Neutrophil Orientation in the Direction of Chemical Gradients" Biophysical Journal 96:3897-3916 (2009).

(56) References Cited

OTHER PUBLICATIONS

Irimia et al. "Microfluidic system for measuring neutrophil migratory responses to fast switches of chemical gradients" Lab Chip 6:191-198 (2006).
Irimia et al. "Polar stimulation and constrained cell migration in microfluidic channels" Lab Chip 7:1783-1790 (2007).
Irimia et al. "Universal Microfluidic Gradient Generator" Analytical Chemistry 78(10):3472-3477 (2006).
Irimia et al., "Cell handling using microstructured membranes," Lab Chip., 6(3):345-52. Epub Feb. 8, 2006.
Jones et al., "Microfluidic chambers for monitoring leukocyte trafficking and humanized nano-proresolving medicines interactions," Proc Natl Acad Sci U S A., 109(50):20560-20565, Epub Nov. 26, 2012.
Jones et al., "Spontaneous neutrophil migration patterns during sepsis after major burns," PloS One, 2014, 9(12): el14509.
Keenan and Folch, "Biomolecular gradients in cell culture systems" Lab Chip 8:34-57 (2008).
Keenan et al. "Microfluidic 'jets' for generating steady-state gradients of soluble molecules on open surfaces" Applied Physics Letters 89:114103 (2006) (3 pages).
Kotz et al., "Clinical microfluidics for neutrophil genomics and proteomics," Nat Med., 16(9):1042-1047, Epub Aug. 29, 2010.
Kuntz and Saltzman, "Neutrophil Motility in Extracellular Matrix Gels: Mesh Size and Adhesion Affect Speed of Migration" Biophysical Journal 72:1472-1480 (1997).
Kurihara et al., "Resolvin D2 restores neutrophil directionality and improves survival after burns," FASEB J., 27(6):2270-2281, Epub Feb. 21, 2013.
Lammermann et al. "Rapid leukocyte migration by integrin-independent flowing and squeezing" Nature 453:51-55 (2008).
Lee et al. "Three-dimensional micropatterning of bioactive hydrogels via two-photon laser scanning photolithography for guided 3D cell migration" Biomaterials 29:2962-2968 (2008).
Levy et al. "Endoscopic ultrasound fine-needle aspiration detection of extravascular migratory metastasis from a remotely located pancreatic cancer" Clin Gastroenterol Hepatol. 7:246-248 (2009).
Lugassy and Barnhill "Angiotropic melanoma and extravascular migratory metastasis: A review" Adv Anat Pathol. 14:195-201 (2007).
Lyons et al., "Microarray analysis of human leucocyte subsets: the advantages of positive selection and rapid purification," BMC Genomics., 8:64, Mar. 5, 2007.
Malawista et al. "Random locomotion and chemotaxis of human blood polymorphonuclear leukocytes from a patient with leukocyte adhesion deficiency-1: Normal displacement in close quarters via chimneying" Cell Motil. Cytoskeleton 46:183-189 (2000).
Mankovich et al., "Differential effects of serum heat treatment on chemotaxis and phagocytosis by human neutrophils," PLoS One., 8(1):e54735, 12 pages, Epub Jan. 22, 2013.
Nauseef, "Isolation of human neutrophils from venous blood," Methods Mol Biol., 412:15-20, 2007.
Office Action in U.S. Appl. No. 13/257,464, dated Aug. 26, 2013, 13 pages.
Office Action in U.S. Appl. No. 13/407,596, dated Mar. 26, 2014, 22 pages.
Office Action in U.S. Appl. No. 15/023,588, dated Feb. 4, 2019, 12 pages.
Office Action in U.S. Appl. No. 15/023,588, dated Jul. 23, 2018, 12 pages.
Overall and Lopez-Otin "Strategies for MMP inhibition in cancer: Innovations for the post-trial era" Nat Rev Cancer 2:657-672 (2002).
Palabrica et al., "Leukocyte accumulation promoting fibrin deposition is mediated in vivo by P-selectin on adherent platelets," Nature., 359(6398):848-851, Oct. 29, 1992.
Partial Supplementary Search Report in European Application No. 17793545.9, dated Apr. 26, 2019, 11 pages.
Phillipson et al., "The neutrophil in vascular inflammation," Nat Med., 17(11):1381-1390, Nov. 7, 2011.
Raeber et al. "Molecularly engineered PEG hydrogels: a novel model system for proteolytically mediated cell migration" Biophysical Journal 89:1374-1388 (2005).
Rhee et al. "Microtubule function in fibroblast spreading is modulated according to the tension state of cell-matrix interactions" Proc Natl Acad Sci USA 104(13):5425-5430 (2007).
Sackmann et al., "Microfluidic kit-on-a-lid: a versatile platform for neutrophil chemotaxis assays," Blood., 120(14):e45-53, Epub Aug. 22, 2012.
Sahai "Illuminating the metastatic process" Nature Reviews Cancer 7:737-749 (2007).
Sahai and Marshall "Differing modes of tumour cell invasion have distinct requirements for Rho/ROCK signalling and extracellular proteolysis" Nat Cell Biol. 5(8):711-719 (2003).
Sahai et al. "Simultaneous imaging of GFP, CFP and collagen in tumors in vivo using multiphoton microscopy" BMC Biotechnology 5(14):1-9 (2005).
Savage et al. "Why does cytotoxic chemotherapy cure only some cancers?" Nat Clin Pract Oncol. 6:43-52 (2009).
Smith et al., "Interplay between shear stress and adhesion on neutrophil locomotion," Biophys J., 92(2):632-640, Epub Oct. 27, 2006.
Sporn "The war on cancer" Lancet. 347:1377-1381 (1996).
Sugarbaker et al. "Gastrectomy, peritonectomy, and perioperative intraperitoneal chemotherapy: The evolution of treatment strategies for advanced gastric cancer" Semin Surg Oncol. 21:233-248 (2003).
Tan et al. "Mechanisms of transcoelomic metastasis in ovarian cancer" Lancet Oncol. 7:925-934 (2006).
Tanos and Rodriguez-Boulan "The epithelial polarity program: machineries involved and their hijacking by cancer" Oncogene 27:6939-6957 (2008).
Todaro et al. "Initiation of Cell Division in a Contact-Inhibited Mammalian Cell Line" J. Cell and Comp. Physiol. 66:325-333 (1965).
Vermeer et al. "Segregation of receptor and ligand regulates activation of epithelial growth factor receptor" Nature 422:322-326 (2003).
Wang et al. "Reciprocal interactions between beta 1-integrin and epidermal growth factor receptor in three-dimensional basement membrane breast cultures: a different perspective in epithelial biology" Proc Natl Acad Sci USA. 95:14821-14826 (1998).
Warner et al., "Microfluidics-based capture of human neutrophils for expression analysis in blood and bronchoalveolar lavage," Lab Invest, 91(12):1787-1795, Epub Sep. 19, 2011.
Yamada and Cukierman "Modeling tissue morphogenesis and cancer in 3D" Cell 130:601-610 (2007).
Yarrow et al. "A high-throughput cell migration assay using scratch wound healing, a comparison of image-based readout methods" BMC Biotechnology 4(21):1-9 (2004).
Zahm et al. "Cell migration and proliferation during the in vitro wound repair of the respiratory epithelium" Cell Motil. Cytoskeleton 37:33-43 (1997).
EP Extended European Search Report in European Application No. 17793545.9, dated Jul. 31, 2019, 9 pages.

* cited by examiner

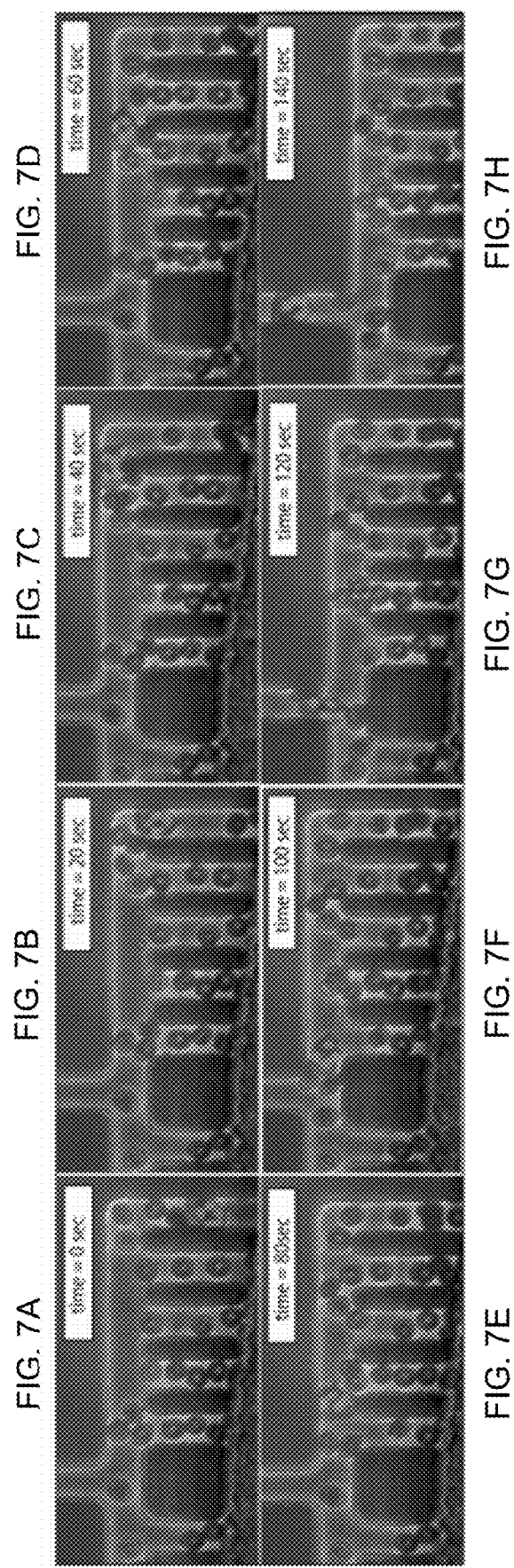

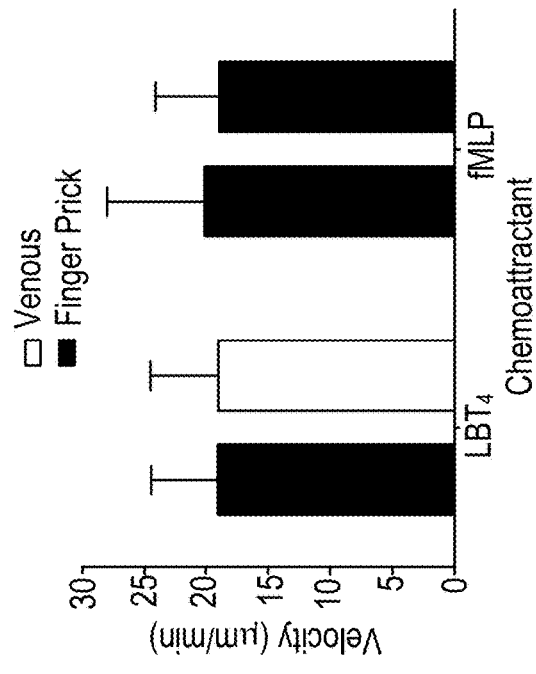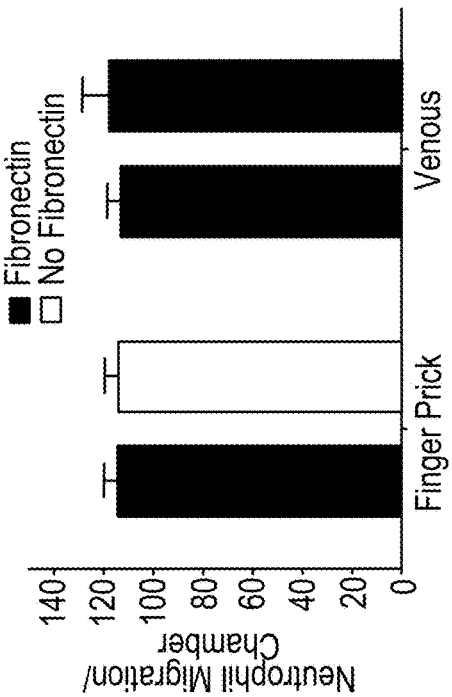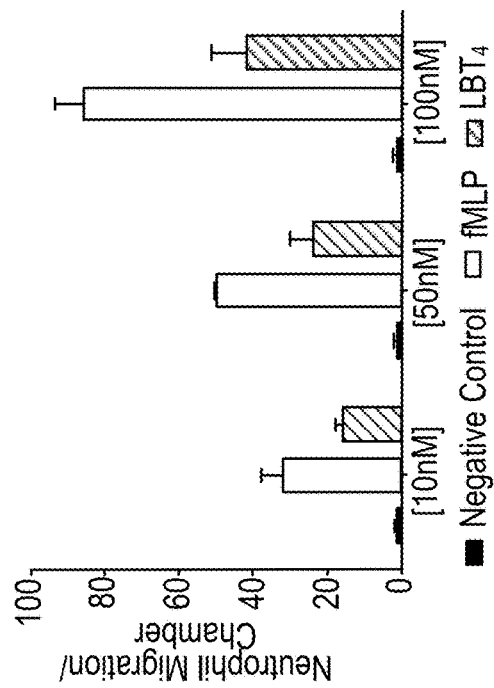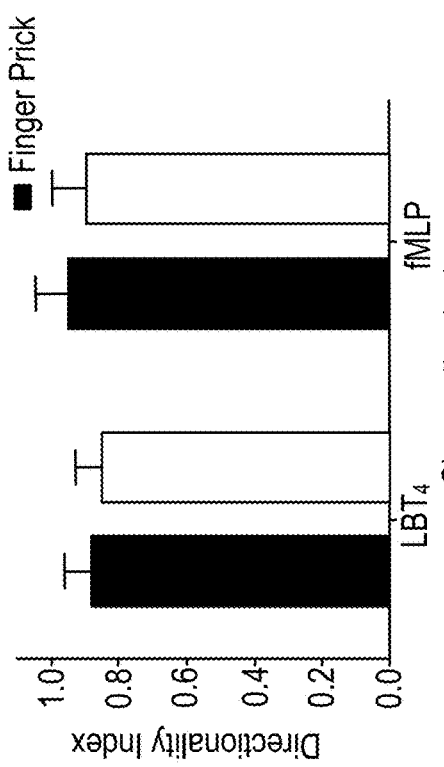

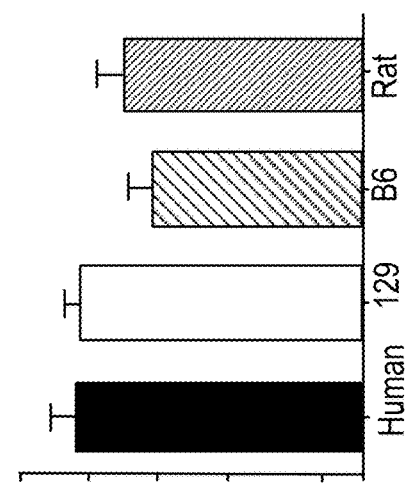
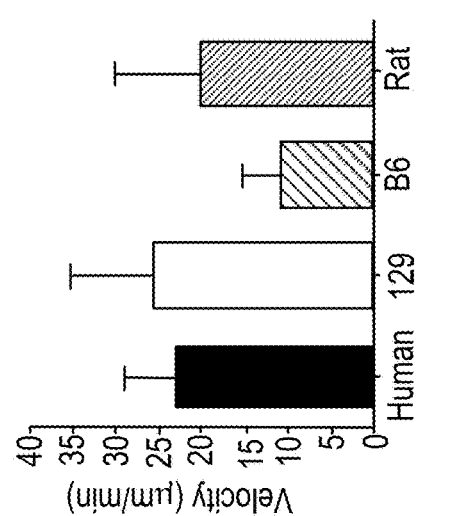
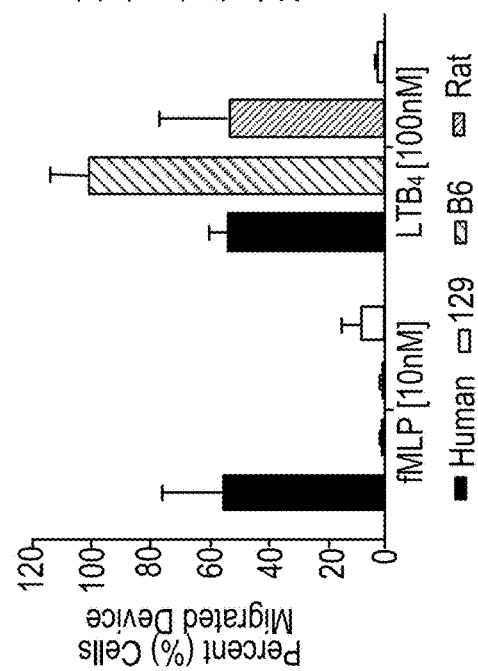
FIG. 11A
FIG. 11B
FIG. 11C

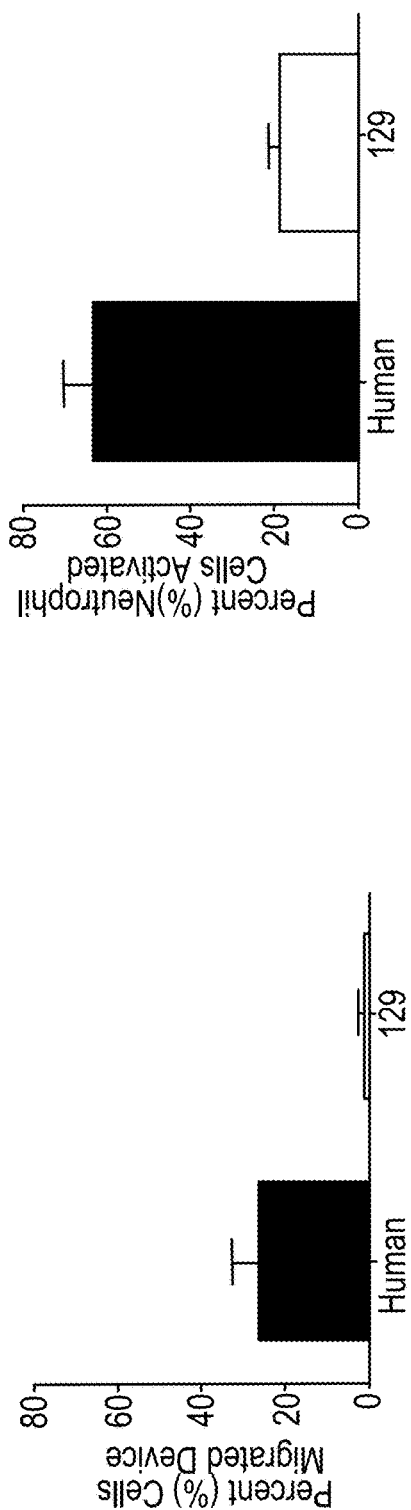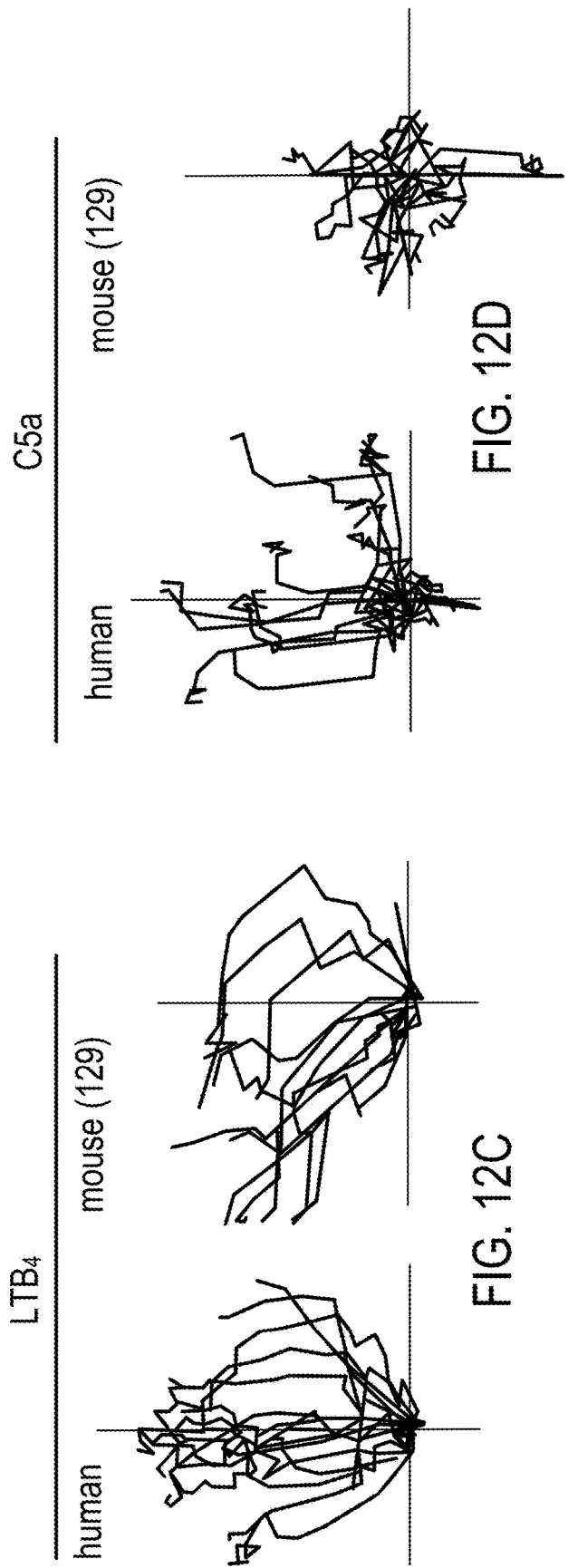

CELL CHEMOTAXIS ASSAYS

CROSS-REFERENCE TO RELATED APPLICATIONS

This application is a Divisional Application of U.S. application Ser. No. 15/023,588, filed on Mar. 21, 2016, which is a U.S. national stage application under 35 USC § 371 of International Application No. PCT/US2014/056614, filed on Sep. 19, 2014, which claims priority to U.S. Provisional Application No. 61/880,591, filed on Sep. 20, 2013, the entire contents of each of which are incorporated herein by reference.

TECHNICAL FIELD

The present disclosure relates to cell chemotaxis assays.

BACKGROUND

Neutrophil directional migration in response to chemical gradients, also known as chemotaxis, is one of the key phenomena in immune responses against bacterial infection and tissue injury. Alterations in neutrophil chemotaxis, e.g., as a result of burns or trauma, may lead to chronic inflammation and further tissue damage. Identifying alterations of neutrophil chemotaxis may help estimate the risk for infections more accurately. To better study neutrophil chemotaxis, in vitro assays have been developed that replicate chemotactic gradients around neutrophils. Since red blood cells out-number neutrophils and have the propensity to clot, measurements of neutrophil migration pattern in whole blood is challenging. For this reason, traditional assays (e.g. transwells) uses isolated neutrophil cells from whole blood.

However, existing assays can include one or more drawbacks. For example, such assays require time-consuming processing of blood to isolate neutrophils. Furthermore, such isolation may alter the responsiveness of neutrophils compared to in vivo conditions, leading to inaccurate characterization of the neutrophils. For instance, certain chemotaxis assays utilize cell separation methods, such as positive selection or negative selection, which are prone to activating neutrophils by engaging specific receptors on the neutrophils. Once activated, the neutrophils' migration profile can be altered; however, this change may not be directly related to the biological condition of interest, but rather a response from the applied stress introduced by cell isolation protocols. Additionally, existing assays require processing relatively large volumes of blood. These assays lack accuracy and/or require use by technicians having specialized training. These limitations, among others, restrict the assays' usefulness in clinical laboratories.

SUMMARY

The microfluidic devices disclosed herein enable the investigation of cell motility, such as neutrophil chemotaxis in blood samples. In particular, the microfluidic devices can be used to measure the directional migration and speed of neutrophils in an attractant gradient, using low sample volumes and with minimal, if any, activation of the neutrophils. Using the new devices, an analysis of cell motility health or impairment, e.g., due to infection or tissue injury, can be determined with a high degree of precision. Moreover, the new devices can be used to identify candidate drug agents suitable for modifying cell motility. Such compounds then can be further screened for their potential use as mediators of inflammation resulting from tissue trauma and/or infections.

In particular, the new devices circumvent the need to use separation methods that interfere with the motile cell analysis (e.g., positive or negative selection) by relying instead on a baffle structure that inhibits the movement of undesired cells in a sample to a greater extent than the movement of the desired motile cells. For neutrophil analysis, the new devices allow whole blood samples to be used directly, and thus reduce the overall sample processing time, while also enabling analysis of the neutrophils directly without the need to isolate them from whole blood.

In general, the subject matter disclosed herein can be embodied in methods for monitoring neutrophil chemotaxis in a device, in which the methods include obtaining a device that includes an input chamber, an attractant chamber, a migration channel arranged in fluid communication between an outlet of the input chamber and an inlet of the attractant chamber, a baffle arranged in fluid communication between the outlet of the input chamber and the migration channel or within the migration channel, and an exit channel in fluid communication with the migration channel at a point beyond the baffle and before the migration channel enters the inlet of the attractant chamber. The methods further include adding an attractant solution to the device to establish an attractant gradient between the input chamber and the attractant chamber, adding to the input chamber a blood sample including a plurality of red blood cells and a plurality of neutrophils, incubating the device under conditions and for a time sufficient to enable movement of cells in the blood sample from the input chamber into the migration channel, in which the baffle is configured to inhibit movement of the red blood cells through the baffle to a greater extent than the baffle inhibits movement of the neutrophils through the baffle, and monitoring whether any of the neutrophils follow the attractant gradient in the migration channel toward the attractant chamber.

The methods can include one or more of the following features in various combinations. For example, in some implementations, the blood sample is whole blood.

In some implementations, monitoring whether any of the neutrophils follow the attractant gradient includes determining a number of neutrophils that follow the attractant gradient.

In certain instances, the blood sample has a volume less than about 2 microliters.

In some cases, establishing the attractant gradient includes adding the attractant solution to all chambers and channels in the device, and replacing the attractant solution in the input chamber with a liquid medium that lacks the attractant such that the attractant gradient forms between the input chamber and the attractant chamber.

In some implementations, the attractant solution includes interleukin-8 (IL-8), C5a, formyl-methionyl-leucyl-phenylalanine (fMLP), leukotriene B4 (LTB4), adenosine triphosphate (ATP), tumor growth factor beta (TGFb), or endothelial derived neutrophil attractant factor (ENA).

In some instances, the baffle includes a first fluid passage in fluid communication with a second fluid passage, in which an angle between a sample transport path in the first fluid passage and a sample transport path the second fluid passage is greater than or equal to about 45 degrees. For example, the angle can be about 90 degrees.

In some implementations, a cross-sectional area of the first fluid passage normal to the sample transport path in the first fluid passage is greater than a red blood cell cross-sectional area, a height of the cross-sectional area is greater than a red blood cell thickness and less than a red blood cell diameter, and a width of the cross-sectional area is greater than the red blood cell diameter. For example, the height of the cross-sectional area can be greater than about 2 microns and less than about 6 microns, and the width of the cross-sectional area can be greater than about 6 microns.

In certain implementations, the baffle includes multiple first fluid passages, and multiple second fluid passages, each first fluid passage being in fluid communication with the output of the input chamber and in fluid communication with a corresponding second fluid passage, in which an angle between a fluid transport path of each first fluid passage and a sample transport path of the corresponding second fluid passage is greater than or equal to about 45 degrees.

In some implementations, the methods further include analyzing the health of the neutrophils that follow the attractant gradient in the migration channel toward the attractant chamber. Analyzing the health of the neutrophils can include determining a number of the neutrophils that follow the attractant gradient toward the attractant chamber compared to a total number of cells moving through the migration channel, determining a rate at which one or more neutrophils follow the attractant gradient toward the attractant chamber, and/or determining a number of neutrophils that do not follow the attractant gradient compared to the total number of moving cells.

In some cases, monitoring whether any of the neutrophils follow the attractant gradient includes obtaining an image of neutrophils in the attractant chamber. Monitoring whether any of the neutrophils follow the attractant gradient can occur for at least 10 minutes.

In some implementations, adding the attractant solution to establish the attractant gradient includes applying a vacuum to the input chamber, the migration channel, the baffle and the attractant chamber such that air is absorbed through walls of the device.

In another aspect, the subject matter of the disclosure can be embodied in methods of screening neutrophil attractants, in which the methods include obtaining a device that includes an input chamber, multiple attractant chambers, and multiple filtration passageways, each filtration passageway being in fluid communication with the input chamber and a corresponding attractant chamber, and each filtration chamber including a migration channel in fluid communication between an outlet of the input chamber and an inlet of the corresponding attractant chamber, a baffle arranged in fluid communication between the outlet of the input chamber and the migration channel or within the migration channel, and an exit channel in fluid communication with the migration channel at a point beyond the baffle and before the migration channel enters the inlet of the corresponding attractant chamber. The methods further includes adding a different attractant solution to at least two attractant chambers to establish a different attractant gradient between the input chamber and each attractant chamber to which an attractant solution has been added, adding to the input chamber a blood sample including multiple red blood cells and multiple neutrophils, incubating the device under conditions and for a time sufficient to enable movement of cells in the blood sample from the input chamber into one or more filtration passageways, in which the baffles of the one or more filtration passageways are configured to inhibit movement of the red blood cells through the baffles to a greater extent than the baffles inhibit movement of the neutrophils through the baffles, and monitoring whether any of the neutrophils follow any of the established attractant gradients to one of the attractant chambers to which an attractant solution has been added.

The methods can include one or more of the following features in various combinations. For example, in some implementations, monitoring whether any of the neutrophils follow any of the established attractant gradients includes, for each different attractant gradient, determining a number of neutrophils that follow the attractant gradient and/or determining a rate at which one or more neutrophils follow the attractant gradient.

In some implementations, the methods further include identifying the attractant that establishes the attractant gradient resulting in the largest number of neutrophils reaching an attractant chamber and/or resulting in the highest rate at which one or more neutrophils follow the attractant gradient. Each baffle can include multiple first fluid passages being in fluid communication with the output of the input chamber, and multiple second fluid passages, each second fluid passage being in fluid communication with a corresponding first fluid passage of the baffle, in which an angle between a fluid transport path of each second fluid passage and a sample transport path of the corresponding first fluid passage is greater than or equal to about 45 degrees.

In some cases, a cross-sectional area of each first fluid passage is greater than a red blood cell cross-sectional area, a height of the cross-sectional area for each first fluid passage is greater than a red blood cell thickness and less than a red blood cell diameter, and a width of the cross-sectional area is greater than the red blood cell diameter.

In another aspect, the subject matter of the present disclosure can be embodied in a device or devices that include an input chamber, an attractant chamber, a migration channel arranged in fluid communication between an outlet of the input chamber and inlet of the attractant chamber, a baffle arranged in fluid communication between the outlet of the input chamber and the migration channel or within the migration channel, and an exit channel in fluid communication with the migration channel at a point beyond the baffle and before the migration channel enters the inlet of the attractant chamber. The baffle is configured to inhibit movement of a first type of cell through the baffle to a greater extent than the baffle inhibits movement of a second type of cell through the baffle.

The device or devices may include one or more of the following features in various combinations. For example, in some implementations, the baffle includes a first fluid passage in fluid communication with a second fluid passage, in which an angle between a sample transport path in the first fluid passage and a sample transport path the second fluid passage is greater than or equal to about 45 degrees. For example, the angle can be about 90 degrees.

In some implementations, a cross-sectional area of the first fluid passage normal to the sample transport path in the first fluid passage is greater than a cross-sectional area of the first type of cell, a height of the cross-sectional area is greater than a thickness of the first type of cell and less than a diameter of the first type of cell, and a width of the cross-sectional area is greater than the diameter of the first type of cell. The height of the cross-sectional area can be greater than about 2 microns and less than about 6 microns, and wherein the width of the cross-sectional area can be greater than about 6 microns.

In some cases, a volume of the input chamber is greater than about 1 microliter and less than about 5 microliters.

In some implementations, a length of a fluid transport path through the migration channel is between about 10 microns and about 2000 microns.

In certain cases, the baffle multiple first fluid passages, and multiple second fluid passages, each first fluid passage being in fluid communication with the output of the input chamber and in fluid communication with a corresponding second fluid passage, in which an angle between a fluid transport path of each first fluid passage and a sample transport path of the corresponding second fluid passage is greater than or equal to about 45 degrees.

In some implementations, the inlet chamber and/or the migration channel is coated with a protein. In some cases, the protein is configured to prevent neutrophil adhesion. The protein can be albumin. In some cases, the protein is configured to promote neutrophil activation. The protein can be P selectin.

In another aspect, the subject matter of the present disclosure can be embodied in a system that includes any of the foregoing devices and a control apparatus configured to image a number of cells migrating from the input chamber through the baffle and the migration channel to the attractant chamber As used herein, "motility" means the ability of a motile cell to move itself, e.g., at a specific migration rate, at least under certain conditions. Motile cells include neutrophils and other immune cells such as granulocyte, monocytes, and lymphocytes, as well as certain cells that can move only under certain specific conditions, such as mast cell precursors, fibroblasts, and endothelial cells (e.g., circulating endothelial cells ("CEC")) or cells under pathological conditions, such as metastatic cancer cells (e.g., circulating tumor cells ("CTC")). Other examples of motile cells include, but are not limited to, sperm cells, bacteria, parasites (e.g., sporozoite phase parasites), eosinophil cells, dendritic cells, and platelets.

As used herein, "chemotaxis" means a movement of a motile cell in response to a chemical stimulus.

As used herein, "attractant" means an agent or force that induces a motile cell to migrate towards the agent. Any agent that activates migration may be used as an attractant, including, for example, agents that introduce a force that is chemically, mechanically, or electrically based.

As used herein, "repellant" means an agent that induces a motile cell to migrate away from the agent. Any agent that activates migration may be used as a repellant, including, for example, agents that introduce a force that is chemically, mechanically, or electrically based.

As used herein, "gas-permeable" means having openings that allow gas to pass through.

As used herein, "blood sample" means any treated or non-treated blood.

Implementations of the subject matter described herein can include several advantages. For example, in some instances, the presently described techniques bypass the need to purify/isolate motile cells from a fluid sample, such as neutrophils from whole blood, prior to performing an assay. In certain implementations, the microfluidic devices disclosed herein enable identification of motile cells, such as neutrophils, without requiring the use of cumbersome cell separation methods such as density gradients, positive selection, or negative selection, which can introduce artifacts by activating neutrophils. The presently disclosed methods do not require a washing step to wash blood from the device after neutrophils are identified. Since such washing steps typically require additional hardware external to the microfluidic device, cost and complexity can be reduced. Neutrophil migration in the presently disclosed devices takes place inside three-dimensional channels, as opposed to solely on a two-dimensional surface, which may induce changes in speed and direction. Thus, the present device enables accurate quantification of neutrophil migration. In some cases, useful quantitative data can be obtained just by counting motile cells that reach an attractant chamber at the end of the assay, as opposed to requiring cell tracking.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIGS. 7A-7H are time-lapse images of a microfluidic device through which red blood cells and neutrophils migrate.

FIG. 9A is a plot of the dose-response of neutrophils migrating out of whole blood to the leukotriene B4 (LTB4) and N-formyl-methionyl-leucyl-pheylalanine (fMLP) chemoattractants.

FIG. 9B is a plot of neutrophil velocity in response to LTB4 and fMLP chemoattractants for venous blood and finger prick blood.

FIG. 9C is a plot that shows a directionality index for neutrophils in response to both fMLP and LTB4.

FIG. 9D is a plot that shows a neutrophil count in the fMLP attractant chamber for pin prick and venous blood in response to attractant with and without fibronectin.

FIG. 11A is a plot of the percentage of cells that have migrated to LTB4 compared with fMLP for human, rat, and mouse cell strains.

FIG. 11B is a plot of cell migration velocity for each different cell strain.

FIG. 11C is a plot of directionality index for each different cell strain.

FIG. 12A is a plot of the percentage of human and mouse cells that have migrated in response to C5a.

FIG. 12B is a plot of the percentage of neutrophil cells activated in response to C5a.

FIG. 12C is a directionality plot of human and mouse cells towards C5a.

FIG. 12D is a directionality plot of human and mouse cells towards LBT4.

DETAILED DESCRIPTION

Figure 1A:
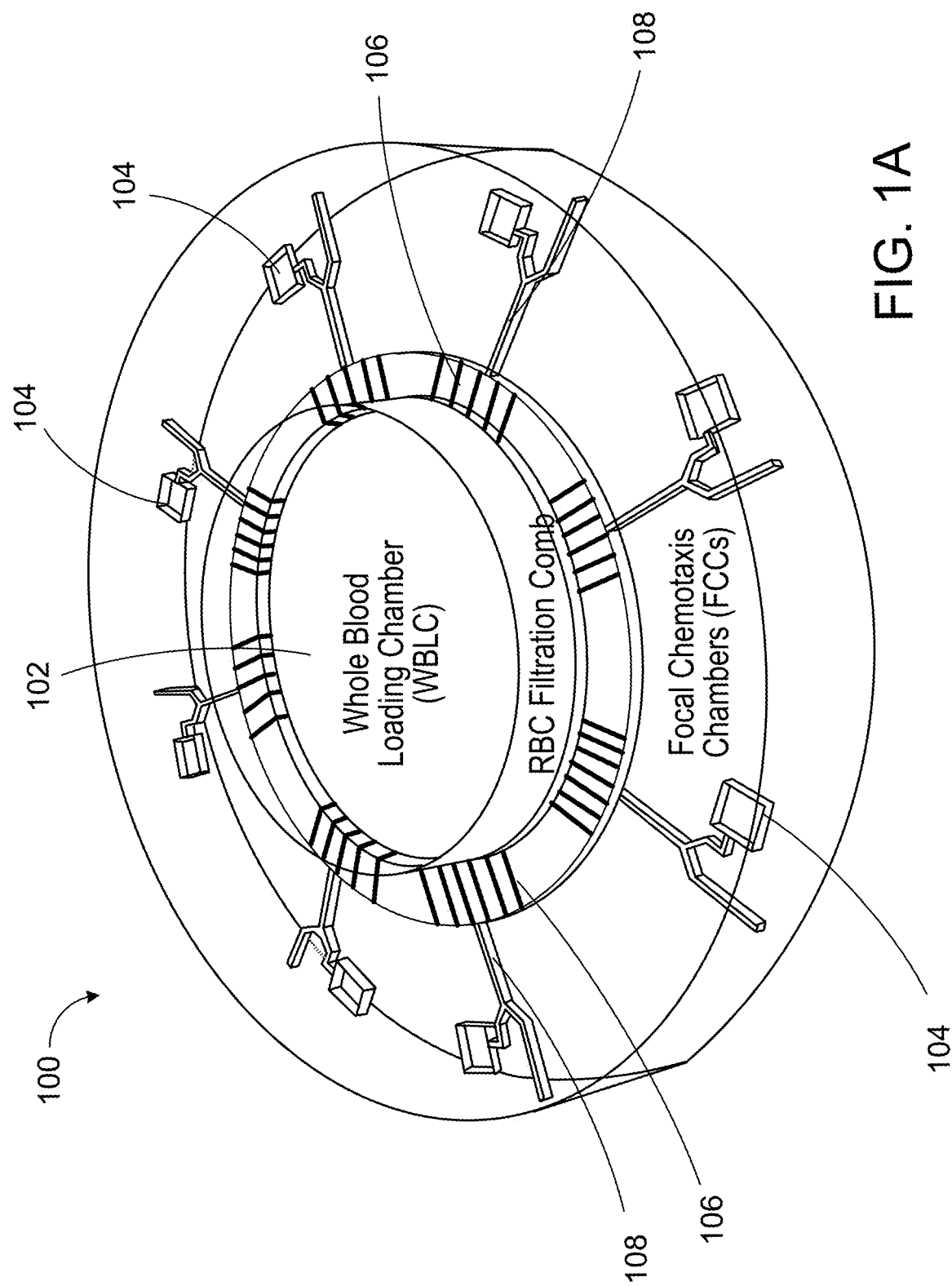
FIG. 1A is a schematic example of a microfluidic device as described herein.

FIG. 1A is a schematic example of a microfluidic device 100 for analyzing cell motility, e.g., neutrophil motility. The microfluidic device 100 can be used for inducing migration of motile cells in an attractant gradient. The device 100 includes an input chamber 102 for receiving a fluid sample, where the fluid sample may contain multiple motile cells and non-motile cells. For example, the fluid sample could be a droplet of whole blood that contains both neutrophils and red blood cells (RBCs). As shown in the example of FIG. 1A, the input chamber 102 is surrounded by one or more attractant chambers 104, in which a motile cell attractant may be provided. Each of the attractant chambers 104 is fluidly coupled to the input chamber 102 through a baffle 106 and a fluid migration channel 108. In the present example, the input chambers 102 have a circular profile, though other shapes may also be used. The diameter of the input chamber 102 can be between about 100 microns to about 2000 microns. For example, the diameters can be about 200, 250, 300, 350, 400, 450, 500, 750, or 1000 microns. If the diameter is too large, it will increase the time required for the motile cells, e.g., neutrophils, far from the baffle 106 to exit the loading chamber and enter the next part of the device.

The input chamber 102 can have a volume in the range of about 1 microliter to about 20 microliters. For example, the input chamber 102 can have a volume of about 2, 3, 4, 5, 7, 8, 10, 12, 15, 18, or 20 microliters. The one or more attractant chambers 104 have rectangular shaped profiles in the present embodiment, but other shapes can also be used. The volume of the attractant chambers 104 can be between about 10-1000 nanoliter. For example, the volume of the attractant chamber can be about 50 to 750 nanoliters, or 100 to 500 nanoliters.

Figure 1B:
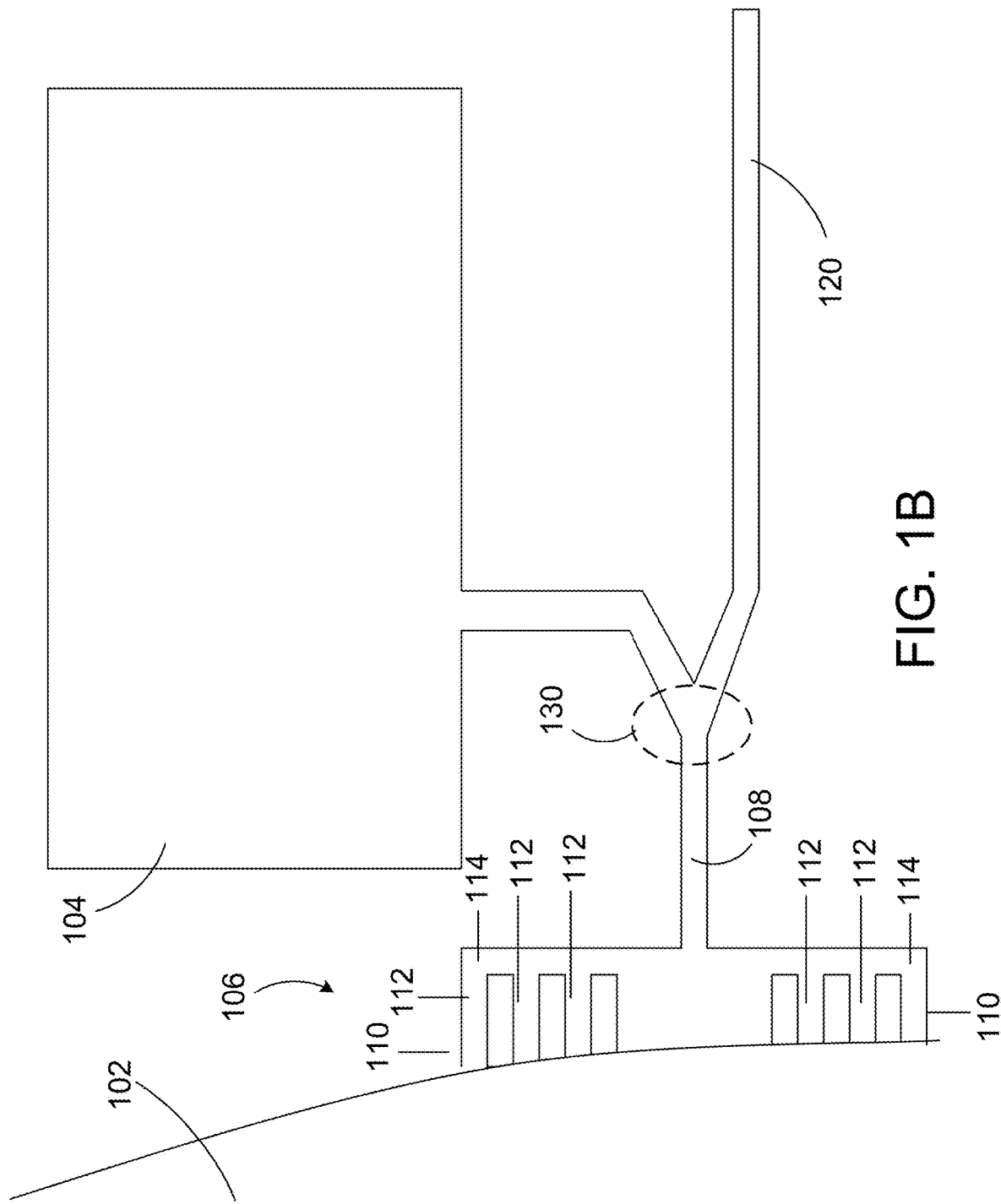
FIG. 1B is a close-up view of a portion of the device of FIG. 1A.

FIG. 1B is a close-up view of a portion of the device of FIG. 1A, showing one of the attractant chambers 104 and the corresponding baffle 106 and migration channel 108 to which the attractant chamber 104 is coupled. As shown in FIG. 1B, the baffle 106 is arranged in fluid communication between an outlet of the input chamber 102 and the migration channel 108, such that a fluid sample deposited in the input chamber can move through the baffle 106 into the migration channel 108. The migration channel 108 is arranged in fluid communication between an outlet of the baffle 106 and an inlet of the attractant chamber.

During operation of the device 100, an attractant solution is added to the attractant chamber 104 to establish an attractant concentration gradient between the input chamber 102 and the attractant chamber 104. In general, the concentration of the attractant is highest in the attractant chamber 104 and decreases from the chamber 104 through the migration channel 108 and the baffle 106 to the input chamber 102. When a fluid sample containing a motile cell responsive to the attractant is added to the input chamber 102, the attractant concentration gradient induces chemotaxis of the motile cell toward the region where the concentration of the attractant is highest, i.e., the attractant chamber 104. Both the baffle 106 and the migration channel 108 are sized to allow the desired motile cell to pass from the input chamber 102 to the attractant chamber 104.

After establishing the attractant gradient, the input chamber 102 is filled with the fluid sample. Cells within the fluid sample begin moving toward the openings of the baffle(s) 106. Cell movement does not occur based on external pressure source (e.g., introducing pressure differences using syringe pumps or liquid pumps) or any flow of the liquid within the device. Instead, cell movement through the fluid in the device is the result of a combination of passive factors including a static pressure difference created by filling the input chamber with the fluid sample, natural diffusion, and/or random Brownian motion. The primary mechanism for motion of motile cells (e.g., by "crawling" in the case of neutrophils or swimming for other motile cells such as certain bacteria and sperm) in the fluid sample will be in response to the existence of an attractant gradient, depending on the choice of the attractant, e.g., chemoattractant.

As explained above, to help prevent the undesired cells from inhibiting or interfering with the active migration of the motile cells, the baffle 106 is configured to inhibit the movement of undesired cells to a greater extent than the desired motile cells. For example, in the device 100 shown in FIG. 1B, the baffle 106 includes one or more passageways 110 sized to selectively allow migration of the desired motile cells, while being small enough to substantially block the movement of other undesired motile and non-motile cells into the migration channel 108. For instance, for neutrophil analysis in a whole blood sample, the dimensions of the passageways 110 are sized to allow migration of neutrophils in the blood sample, while being small enough to substantially impede the passage of other cells in the sample, such as RBCs and other leukocytes (e.g., monocytes and lymphocytes). While neutrophils are generally the same size or larger than RBCs and other leukocytes (e.g., a typical human neutrophil is between about 8-15 microns in diameter; typical human lymphocytes and monocytes have diameters of about 7 microns and between about 10-30 microns, respectively; a typical disc-shaped human RBC has a diameter between about 6-8 microns and a height between about 2-2.5 microns), neutrophils are more deformable in shape than RBCs and other blood cells, and thus can change dimensions to migrate through tight passages that would otherwise impede the movement of other leukocytes and RBCs.

One way of appropriately sizing the passageways 110 to allow neutrophils, but not other cells to pass through is to restrict the cross-sectional area of the passageway along a plane normal to the direction of cell movement. For example, one could use microfluidic channels having cross sections smaller than that of the undesired cells. However, such channels could be completely obstructed at their entrance by a collection of cells, precluding the formation of gradients. Furthermore, cross-sectional areas that are smaller than that of the undesired cells could also impede the desired motile cell migration, since such cells would have no gaps to pass through. Instead, for the microfluidic devices disclosed herein, the cross-sectional areas of the passageways 110 and/or of the migration channels 108 are configured to be larger than the largest diameter or cross-sectional dimension of one or more of the different undesired cells. At the same time, a first dimension of the passageway and/or migration channel cross-section is configured to be about equal to or less than a size of the undesired cell. With this configuration, substantial movement of the undesired cell(s) through the passageway 110 is still be restricted, but the desired motile cell (e.g., neutrophil) modifies its shape as it follows the attractant gradient so as to migrate around and between the undesired cells through open gaps in the passageway 110. The desired motile cells thus "squeeze" their way around and between the undesired cells. As an example, a first dimension of the cross-section (e.g., width) can be set larger than the cell(s) to be blocked, whereas a second dimension of the cross-section (e.g., height) is set to be shorter than the cell(s) to be blocked.

Figure 2:
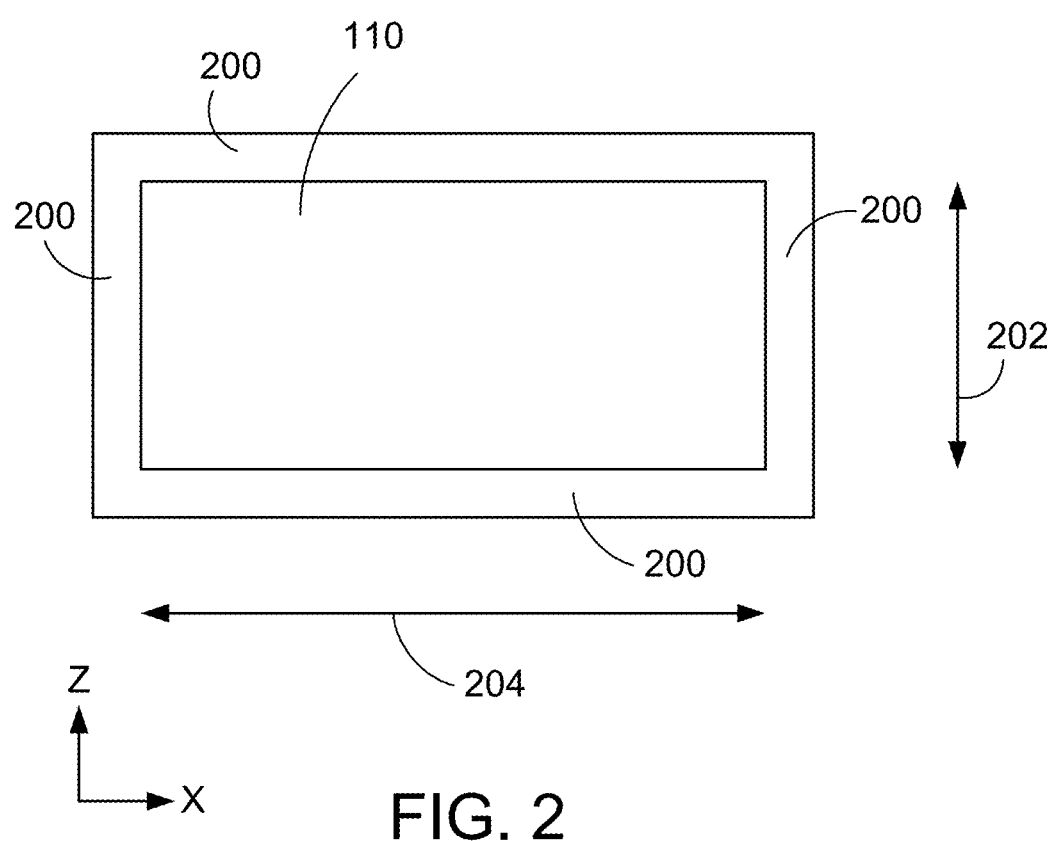
FIG. 2 is a schematic depicting an example of a baffle passageway cross-section.

FIG. 2 is a schematic depicting an example of a passageway cross-section along a plane that is normal to a direction of transport through the passageway 110 (the direction of transport in this example is along the y-direction into the page). The cross-section is bound by walls 200 of the passageway 110. For separating RBCs and undesired leukocytes from neutrophils in a human blood sample, the height 202 of the passageway 110 is configured to be less than the diameter of a RBC, e.g., between about 1-6 microns. Additionally, the width 204 of the passageway 110 is configured to be larger than the diameter of the RBC, e.g., between about 8-12 microns. With such dimensions, the device tends to force RBCs tend to lay on their side before entering the passageway 110, thus limiting RBC passage. Furthermore, monocytes and lymphocytes tend to require much larger openings (e.g., at least 10 microns by 10 microns) to allow migration. However, given the relatively large passageway width, there is still room for the neutrophils to migrate past the RBCs and other leukocytes. Furthermore, the larger width prevents complete clogging of the passageway 110 by the RBCs and other leukocytes. If the channel cross-section is too small (e.g., less than 1 μm), gaps do not form such that the attractant gradient cannot be maintained and the neutrophils do not have enough room, even after deforming their shape, to pass through into the migration channel 108. The cross-sectional area of the passageways 110 can be smaller or larger than those described here, and can be used to analyze the migration of cells other than neutrophils including, for example, lymphocytes, monocytes, natural killer lymphocytes, platelets and megacariocytes, epithelial cells, endothelilal cells, cancer cells, bacteria, sperm, and the like. Table 1 provides a list of different examples of motile blood cells, their typical concentration in human blood, and an appropriate cross-sectional area of a rectangular shaped channel for allowing migration of the motile cells. Table 1 also lists channel cross-sectional areas for other motile cells such as bacteria, parasites and sperm cells. The device can also be used with cells from blood of other animals, e.g., murine, rabbit, monkey, or canine blood, as well. However, the dimensions of the passageways 110 should be modified to accommodate the different sizes of cells obtained from these other types of blood. For example, neutrophils and RBCs from murine blood are smaller than those of humans (murine RBC are about 5-6 μm in diameter which humans are about 7 μm, and murine neutrophils cell diameter ranges 5-6 μm while human neutrophil cell diameter ranges 7-8 μm).

TABLE 1

| Blood Cell Type | Cells/μL blood - healthy individual | Typical channel size for migration |
|---|---|---|
| Neutrophil (granulocyte) | 5,000 | 6 × 6 μm$^2$ |
| Eosinophil | 10 | 6 × 6 μm$^2$ |
| Monocyte | 50 | 10 × 10 μm$^2$ |
| Lymphocyte | 3,000 | 8 × 8 μm$^2$ |
| Dendritic Cell | 1 | 10 × 10 μm$^2$ |
| Circulating endothelial cell | 0.1 | 10 × 10 μm$^2$ |
| Fibrocyte | 0.1 | 6 × 6 μm$^2$ |
| Mast cell | 0.1 | 6 × 6 μm$^2$ |
| Circulating tumor cell | 0.01-1 | 10 × 10 μm$^2$ |
| Platelets | 50,000 | 2 × 2 μm$^2$ |
| Other motile cells in complex mixtures | | |
| Bacteria | | 1 × 1 μm$^2$ |
| Parasites (sporozoite phase) | | 5 × 5 μm$^2$ |
| Sperm cells | | 2 × 2 μm$^2$ |

The movement of undesired cells relative to the movement of desired motile cells also can also be restricted by adding a relatively sharp turn in the passageway 110, e.g., a turn of at least about 90 degrees. Such a turn creates congestion/gridlock in the movement of undesired cells. In particular, as a cell moves, tumbles, floats, or is pushed into the corner, it tends to block the advance of other trailing cells behind it by restricting the cross-section of the channel to less than the diameter of a single cell. This configuration works well for cells that move based on granular flow (e.g., RBCs), because the granular flow force pushing the cells in the channel is not enough to deform the cells through the restricted section. However, since the cross-section of the channel is larger than that of the undesired cell, gaps still exist for the desired motile cells to pass through.

As an example, referring again to FIG. 1B, the passageway 110 is composed of two portions in fluid communication with each other, in which a direction of cell movement in a first portion 112 is angled with respect to a direction of cell movement in the second portion 114. The first portion 112 is in fluid communication with an output of the input chamber 102, whereas the second portion 114 is in fluid communication with an input to the migration channel 108. Preferably, the angle between the directions of cell movement in the two portions is sharp enough to trap the undesired cells and prevent them from dispersing into the migration channel 108. The angle can be measured from a position where the second portion would otherwise be co-linear with the first portion. For example, in the baffle 106, the angle between the direction of cell movement in the first portion 112 and the direction of cell movement second portion 114 is about 90 degrees. Other angles also can be used. For example, the angle can include, but is not limited to, about 45 degrees, about 55 degrees, about 65 degrees, about 75 degrees, about 85 degrees, 105 degrees, 115 degrees, 125 degrees, or 135 degrees. The angle should be at least about 45° to effectively restrict movement of the undesired cells. While the angle between the two portions of the passageway 110 further inhibits the movement of the undesired cells, the desired motile cells can continue to progress toward the attractant gradient by moving through gaps in the passageway 110 left by the undesired cells.

The baffle 106 can include a single passageway 110 or multiple passageways 110, each of which is in fluid communication with the input of the migration channel 108 and each of which is configured to inhibit movement of undesired cells as described above. For example, as shown in FIG. 1B, the baffle 106 includes several passageways 110, with the first portion 112 of each passageway 110 separated by a wall 116, creating a comb-like structure. The baffle 106 may include, but is not limited to, between 5 and 30 passageways, e.g., 20 passageways. As shown in FIG. 1B, the first portion 112 of each passageway 110 may be arranged in parallel with a first portion 112 of an adjacent passageway 110. The second portion 114 of each passageway 110 can be coupled together to form a single horizontal channel. Although each passageway 110 is shown to have a 90 degree turn, different angles can be selected for each passageway as discussed above, and the angles can all be the same or different. The lengths (i.e., the distance along the direction of cell transport) for the first portions 112 can be in the range of between about 10 to about 100 microns. For example, the length can be between about 20 to about 80 microns, between about 30 to about 70 microns, or between about 40 to about 60 microns. Other lengths also are possible. The length of the horizontal channel (formed by the second portions 114 of each passageway 110) can be in the range of about 15 to about 500 microns. For example, the length of the horizontal channel can be between about 50 microns to about 400 microns, between about 100 microns to about 300 microns, or between about 150 microns to about 250 microns. Other lengths also are possible. The width of the walls 116 separating the first portion 112 of each passageway can range from about 5 microns to about 100 microns, e.g., 10 microns.

The device 100 also may include an exit channel 120, e.g., an open-ended channel that exits the device and is open to the fluid media outside the device, in fluid communication with the migration channel 108 at a point beyond the baffle 106 and before the migration channel 108 enters the inlet of the attractant chamber 104. As in the migration channel, the fluid in the exit channel does not move or flow during the monitoring of chemotaxis. The exit channel 120 creates a bifurcation 130 that allows one to monitor the ability of motile cells to follow the attractant gradient toward the attractant chamber. For example, if one or more motile cells migrate towards the exit channel instead of towards the attractant chamber, this may be an indication that the motile cell is damaged or functioning improperly. Thus, the presence of the exit channel allows one to quantify the number of desired cells that correctly follow the attractant gradient, as opposed to moving into the attractant chamber. Alternatively, the migration of motile cells through the exit channel may be an indication that the attractant is inducing chemokinesis and not chemotaxis of the desired cell.

Both the exit channel 120 and the migration channel 108 should be sized to allow at least the desired cells to pass through. For example, the height of the exit channel 120 and/or the migration channel 108 can be between about 1-3 microns, though larger heights also can be used. The lengths (distance along the direction of propagation) of the exit channel 120 and the migration channel 108 can be between about 10-2000 microns, e.g., 75 microns long. The widths of the exit channel 120 and the migration channel 108 can be between about 8-12 microns, though other widths may also be used.

As shown in FIG. 1A, the device 100 of this embodiment includes multiple attractant chambers 104 in fluid communication with the input chamber 102, although a device with a single attractant chamber can be used. If desired, two or more of the attractant chambers 104 may be loaded with different attractants. Accordingly, the effect of different attractants on the directionality and responsiveness of motile cells from a single fluid sample can be studied simultaneously.

In some implementations, the baffle's ability to restrict the movement of undesired cells can be enhanced by adding antibodies to the surfaces enclosing the baffle's passageways. The antibodies can be selected to specifically bind to RBCs (e.g., GlyA+) or other undesired cells (e.g., CD14+ can be used for monocytes), further reducing the number of the undesired cells that pass into the migration channel. In addition, or alternatively, other agents may be added to the baffle surfaces enclosing the passageways. For example, the surfaces can be coated with agents, such as proteins, glycoproteins, or combinations of them. Such coatings can prevent the absorption of soluble factors to the surfaces, and facilitate migration of the desired motile cells and/or impede the movement of undesired cells. With certain motile cells, such as neutrophils, it can be important in certain embodiments not to include any antibodies or other agents in the device that activate the motile cells in a way that can alter their motility.

Other areas of the device may also be coated with agents for facilitating or modifying the motile cell functionality. For example, as an alternative or in addition to coating the baffle, the inlet chamber and/or migration channel can be coated with agents. The agents can include proteins such as albumin for preventing surface adhesion of neutrophil. Alternatively, the protein can be configured to promote neutrophil adhesion, such as P selectin.

In some implementations, a repellant can be used in the device to influence motile cell directionality. For example, a repellant may be added to the exit channel or in a separate repellant chamber that is in fluid communication with the migration channel. Examples of repellants include Slit2, Slit3, high concentrations [mM] of IL-8, Dipeptidyl Peptidase IV, and quorum sensing bacteria. Other chemorepellents are known to affect different types of motile cells and can be selected by those skilled in this field.

Device Fabrication and Assay Preparation and Use

As one example, the microfluidic device 100 can be manufactured using the following methods. First, a mold defining the features of the device 100 is obtained. For example, the mold can be formed by applying and sequentially patterning two layers of photoresist (e.g., SUB, Microchem, Newton, Mass.) on a silicon wafer using two photolithography masks according to known methods. The masks can contain features that define the different aspects of the device 100 such as the input chamber, the baffle, the migration channel, the attractant chamber, and the exit channel. The wafer with the patterned photoresist then may be used as a master mold to form the microfluidic parts. A polydimethylsiloxane (PDMS) solution then is applied to the master mold and cured. After curing, the PDMS layer solidifies and can be peeled off the master mold. The solidified PDMS layer includes grooves and/or recesses corresponding to the passageways, migration channels, exit channels, and attractant chamber of the device 100. In some implementations, the mold pattern is designed to include the features of multiple devices 100. Each device can be cut out from the PDMS layer using, for example, a hole puncher (e.g., a 5 mm hole puncher). Similarly, the input chamber also can be formed by using a smaller hole puncher (e.g., a 1.5 mm diameter hole puncher) to punch out PDMS material from the PDMS layer. The PDMS devices then are bonded to a substrate such as a glass slide or multi-well plate (i.e., each device is positioned in a corresponding well of the well plate). For example, a bottom surface of the PDMS devices can be plasma treated to enhance the bonding properties of the PDMS. The plasma treated PDMS devices then are placed on the glass slide or into the bottom of a well on a plate and heated to induce bonding. The microfluidic channels of the device can also be exposed to plasma treatment prior to bonding to render the channels hydrophilic. Hydrophilic channels can enhance priming of the device with the attractant due to capillary wicking effects. FIG. 1A is a schematic depicting a perspective view of a microfluidic device 100 fabricated according to the foregoing procedures.

The example of a microfluidic device 100 described above, includes a substrate layer of glass and a top layer of PDMS in which the input chamber 102, the baffle 106, the migration channel 108 and the attractant chamber 104 are formed. In other implementations, both the substrate layer and the top layer can be PDMS substrates or other similar materials.

In general, the top layer (or the bottom layer) in which the baffle, migration channel, exit channel and attractant chamber are formed should be selected to have the following characteristics. The layer can be gas-permeable so that air in the baffle, migration channel, and attractant chamber can be displaced through the layer, either by pumping fluid into the device or by placing the device under vacuum. Furthermore, the layer can be transparent so as to facilitate image capture of cell motility within the device. As explained above, the surfaces of the baffle walls enclosing the passageways 110 may be coated with agents, for example, antibodies, to facilitate capture of undesired cells from the fluid sample.

Figure 3:
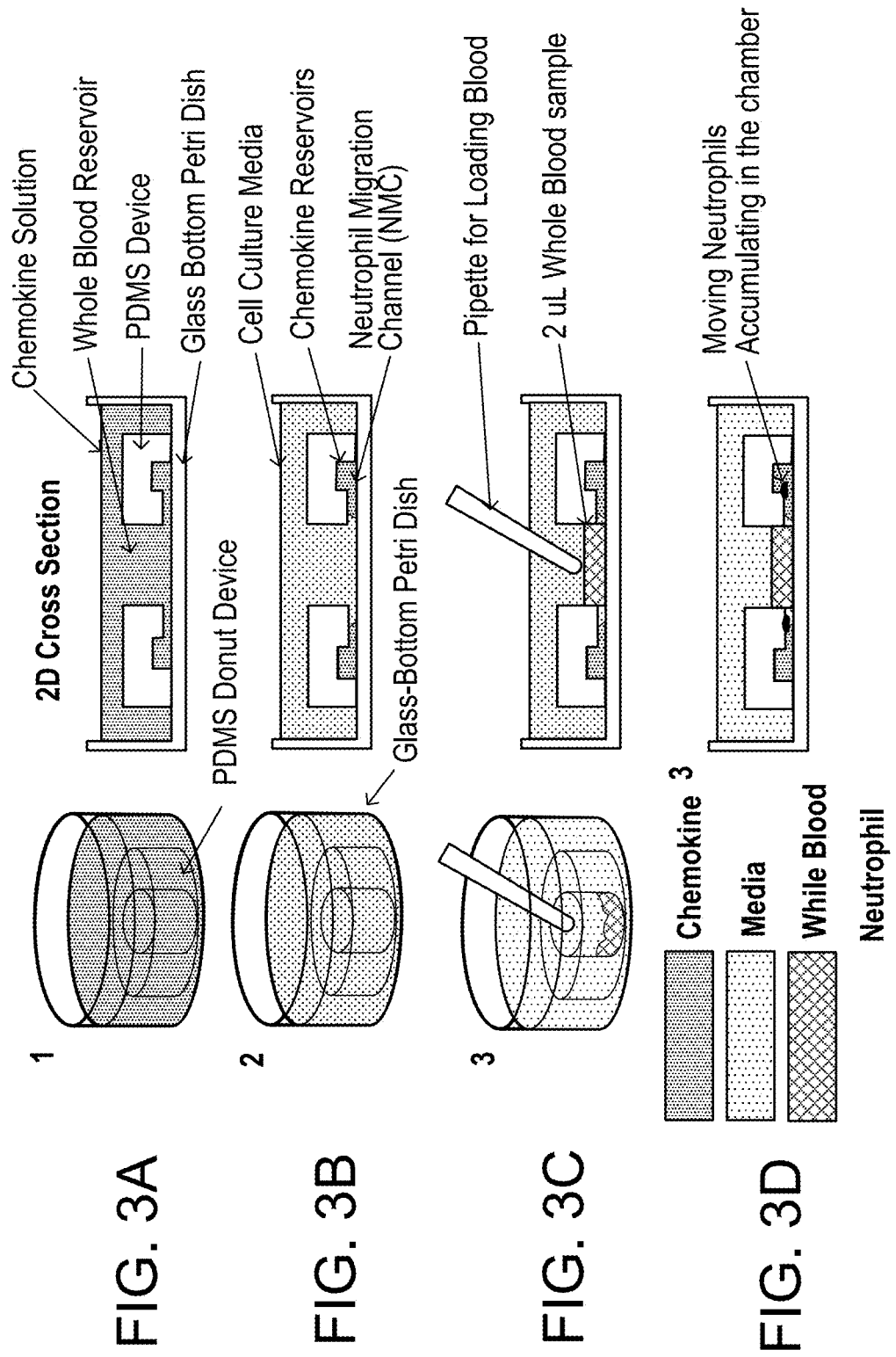
FIGS. 3A-3D depict stages of microfluidic assay preparation.

FIGS. 3A-3D are schematics depicting examples of the different stages in preparing the device 100 for an assay. On the left side of each of FIGS. 3A-3C, the microfluidic device is shown situated in a petri dish. The right side of each of FIGS. 3A-3C depicts a cross-section of the input chamber (labeled "whole blood reservoir"), the migration channel (labeled "neutrophil migration channel"), and the attractant chamber (labeled "chemokine reservoir") of the microfluidic device. Though the figures reference neutrophil migration channel and whole blood reservoir, the process shown is applicable to other motile cells and fluid samples as well. As shown in FIG. 3A, a first stage of assay preparation includes priming the device with an attractant solution (for example, a chemokine solution, as referred to in FIG. 3A). Various attractant solutions can be selected based on the motile cell to be analyzed.

Examples of attractant solutions for neutrophils include N-formyl-methionyl-leucyl-pheylalanine (fMLP), leukotriene B4 (LTB4), interleukin-8 (IL-8), the protein fragment C5a, adhenosine tri-phosphate (ATP), tumor growth factor beta (TGFb), or endothelial derived neutrophil attractant factor (ENA), or the like. In some implementations, the attractant solution includes the extracellular matrix protein fibronection to promote neutrophil surface adhesion. Preferably, the attractant solution is added shortly after performing plasma treatment and bonding the device so that the hydrophilic property of the microfluidic channels has not dissipated and can assist priming the channels through capillary effects. Other methods of rendering the inner surfaces of the device hydrophilic can also be used. Other materials that are inherently hydrophilic can also be used to manufacture the device. The attractant solution can be added to the device through the input chamber, e.g., through pipetting using a gel-loading tip and surrounding the circumference of the whole device.

The device 100 then is placed under vacuum. By applying a vacuum to the device 100, the attractant solution is forced completely into the fluidic channels and all chambers of the device 100. At the same time, the vacuum causes any air present in the channels or chambers to diffuse through the gas-permeable material of the top layer (e.g., the PDMS layer). This process removes air bubbles that would otherwise be present in the fluidic channels of the device, and which could potentially block the passage of cells through the baffle and migration channel. To establish the vacuum, the device can be placed into a desiccator, in which air pressure is reduced to a vacuum level of about 17-25 inches of water, for at least about 15 minutes.

In a second stage (FIG. 3B), the device 100 then is removed from the vacuum and the input chamber is washed to remove excess attractant solution. For example, the input chamber can be washed using a phosphate buffer saline (PBS) solution. The attractant solution in the baffle, migration channel, and attractant chamber remains in the device 100. After washing, the wells in which the devices 100 sit are filled with a fluid suspension (referred to as "cell culture media" in FIG. 3B) that is free of the attractant and allowed to sit for a specified time so that a stable attractant gradient can form between the attractant chamber and the input chamber. The exit channel is surrounded by the fluid suspension and therefore acts as a sink for the attractant. Since the gradient in the exit channel decreases away from the migration channel, normal functioning cells will not migrate toward the exit channel. The fluid suspension can include media solutions such as RPMI 1640 media.

After establishing the attractant gradient, the fluid sample of interest is introduced into the input chamber 102 of the device in a third stage (FIG. 3C). For example, using gel-loading tips, samples of whole blood (or samples containing isolated motile cells) can be pipetted into the chamber 102. Once the fluid sample is in place in the chamber 102, static fluid pressure causes some of the cells of the sample to move, e.g., by granular flow (e.g., like grains of sand tumbling down an incline) into the passageways 110 of the baffle 106, where the desired motile cells begin migrating in a direction of the attractant gradient (see, e.g., FIG. 3D). Various properties of the motile cells may be monitored in the device include, for example, the absolute number of desired motile cells that reach the attractant chamber, the number of desired motile cells that reach the attractant chamber relative to the total number of cells (motile and/or non-motile) in the fluid sample, the rate at which the motile cells reach the attractant chamber, and/or the directionality of motile cells in the device 100.

In the case of whole blood, the RBCs will move according to a granular flow pattern. Once the RBCs reach the turns in the passageways 110, the cell movement will slow or stop and cause a backup of trailing cells. In contrast, healthy neutrophils in the sample will continue to follow the attractant gradient and squeeze through openings left by the RBCs in the passageways 110. The healthy neutrophils will then proceed through the migration channel 108 towards the attractant chamber 104. Unhealthy neutrophils may continue migrating into the exit channel 120 or never reach the attractant chamber 104. During the migration assays, the device 100 can be maintained at a temperature suitable for cell migration. For example, in the case of neutrophil migration, the device 100 can be placed in a biochamber and heated to about 37° C. and having a 5% $CO_2$ atmosphere with 80% humidity to maintain the viability of the cells. The humidified environmental chamber can, in certain implementations, increase the observation duration several hours.

Figure 4:
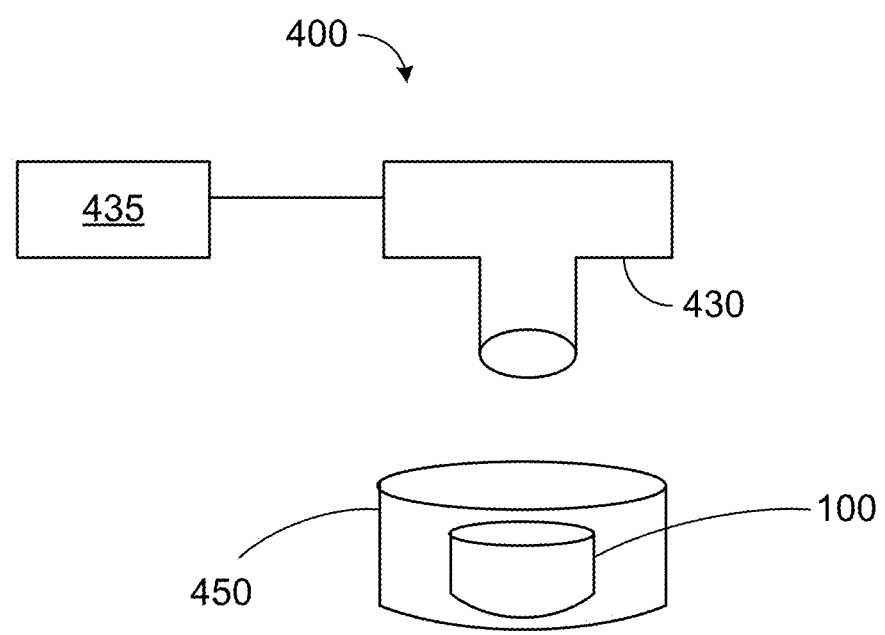
FIG. 4 is a schematic of an example of a system for analyzing an assay performed in a microfluidic device.

FIG. 4 is a schematic of an example of a system 400 for analyzing the properties of motile cells following an attractant gradient, and includes a microfluidic device 100. The microfluidic device 100 includes a baffle for inhibiting the movement of undesired cells in a fluid sample relative to the movement of desired cells, a migration channel, and an attractant chamber for establishing an attractant gradient. The device 100 is held in a container 450, such as a petri dish or the like. The system 400 includes an imaging system 430 configured to capture images and/or video of the cell migration. For example, the imaging system 430 is configured to perform time-lapse imaging. An example of an imaging system suitable for use to record images of the cell migration is the Nikon Eclipse Ti microscope with 10-20× magnification.

The total time required to record the movement of the motile cells toward the attractant chamber depends on various factors, including the baffle passageway length, the migration channel length, the attractant being used, and the attractant gradient itself. Since neutrophils typically require about 5 minutes to begin migration in response to an attractant gradient, a minimum time necessary for monitoring the neutrophil motion with the system 400 is no less than approximately 10 minutes (e.g., a distance of neutrophil migration of about 150-200 µm for a neutrophil migration rate of 18 µm/min). Longer monitoring times also may be required, depending on the nature of the particular assay being conducted. For example, the time to monitor motile cell movement (e.g., neutrophil movement) may be on the order of 20 minutes, 30 minutes, 40 minutes, 50 minutes, 1 hour, or longer. While time-lapse imaging is one particular way for characterizing the cell migration, one could also count the number of cells that reach the attractant chamber at the end of the assay, without the aid of time-lapse imaging.

The system 400 further includes a computer system 435 that is operatively coupled to the imaging system 430. The computer system 435 can include a computer-readable storage medium (for example, a hard disk and the like) that stores computer program instructions executable by data processing apparatus (for example, a computer system, a processor, and the like) to perform operations. The operations can include controlling the imaging system 430 to capture images of the migration of cells through the device toward the attractant chamber. In addition, the computer system 435 can receive the captured images from the imaging system 430, and process the images to obtain various parameters, e.g., one or more of a migration speed of motile cells in a channel, a number of motile cells reaching the attractant chamber, and a directionality of the motile cells. Directionality of motile cells can be quantified by counting the number of motile cells that follow the attractant gradient into the attractant chamber, as opposed to the exit channel.

In some implementations, the computer system 435 is configured to execute computer software applications that perform statistical analysis of the data captured by the imaging system 430. For example, the computer system 435 can be configured to perform multivariate analysis to determine correlations between neutrophil migration speed and clinical parameters. In some implementations, experiments to characterize the formation of gradients inside the device in the absence of motile cells can be performed by replacing all or portions of the attractant solution (for example, the fMLP) with a fluorescent agent (e.g., fluorescein) of comparable molecular weight, and analyzing the distribution and changes in fluorescence intensity from time-lapse imaging using the imaging system 430 and the computer system 435.

Applications

The microfluidic motility assays and methods described herein can be used in various applications. For example, the measurement of neutrophil directionality is important in patients at high risk for infection where directionality of neutrophils is known to be impaired, such as those with burn injuries or tissue trauma, patients undergoing chemotherapy, neonates in intensive care units, and/or diabetics. Impaired and/or over-stimulated neutrophils may migrate away from the site of the injury and therefore cause injury to healthy tissues. The devices disclosed herein provide a platform to analyze neutrophil behavior to determine the extent of damage to the neutrophils. For example, the devices can be used to determine the percentage of neutrophils that behave abnormally, as well as the particular type of abnormal behavior, such as failing to follow an attractant gradient or changes in migration rate. The devices can be used on samples of whole blood without requiring a separate isolation step for the neutrophils, thus reducing processing time. Additionally, the use of whole blood preserves the natural environment for neutrophils without inducing neutrophil activation. The devices can be designed to handle small quantities of fluid sample, e.g., samples having a volume of about 2 microliters, or about 1 microliter. The devices can be used with blood obtained from humans or animal subjects. Both reductions in processing time and reduced sample volume requirements are advantageous for clinical applications, where it may not be feasible to obtain larger amounts of sample fluid, e.g., in infants or small mammals.

In some implementations, the devices can be used to analyze efficacy of one or more medications on neutrophil activity. For example, a medication that affects, e.g., enhances, neutrophil motility can be administered to a subject (e.g., a patient having a burn injury or other tissue trauma) to vary the motility of neutrophils within the subject. The medication can include one or more of several modulators of neutrophil migration such as endogenous modulators (e.g., acetylcholine, interleukin-10 (IL-10), TNFalpha, interleukin-1 (IL-1), interleukin-6 (IL-6)), resolvins, lipoxins, or exogenous modulators (e.g., curcumin, lysophosphatidylglycerol, or cholinergic drugs). Blood samples then can be obtained from the patient once or periodically after administration of the drug. Using the devices and systems described herein, neutrophil activity can be analyzed to determine the drug's effect on neutrophil motility. In some situations, neutrophils obtained from a subject can be studied over a one week period, for example, at 48 hour intervals. To determine a long-term effect of an injury and treatment on the subject, the study period can be expanded to longer periods, e.g., six months, at regular intervals. With respect to neutrophils, an increase in the rate of migration observed over such time intervals may indicate wound healing. If the rate of migration of the neutrophils does not suggest wound healing, then a treatment can be altered to administer a different drug.

The device 100 shown in FIG. 1A includes multiple attractant chambers 104 coupled to a single input chamber 102. Accordingly, the device 100, or similar devices having multiple attractant chambers, can be loaded with multiple attractants (e.g., a different attractant for each attractant chamber) to establish different attractant gradients. Using the systems disclosed herein, one can then analyze the responsivity of motile cells to the different attractant gradients. One can quantify a person's neutrophil functionality after injury or infection (or any perturbation to the immune system) as well as to measure the efficacy of potential drugs or treatments.

Further characterization of neutrophil motility using the microfluidic devices described herein can have important diagnostic implications not only for burn patients, but also for patients afflicted by other diseases that compromise neutrophil functions. For example, the device can be applied to analyze neutrophil motility in pediatric patients to identify patients who are at a higher risk for certain diseases. In transplantations, the device can be used to analyze neutrophil motilities to determine if there is a correlation between neutrophil motility under medication and the occurrence of complications, for example, infections and rejections. By determining a range of neutrophil motilities that correlate to low infection and at which immuno-suppressant functions are not suppressed, it may be possible to vary the quantities of immuno suppressant medication that is being administered to patients.

In some implementations, the devices can be used to screen hundreds, 1000s, 10,000s, or 100,000s of small molecules or other chemical agents for their effect on motile cell motility, e.g., on neutrophil chemotaxis. That is, the devices can be used to screen such compounds to see which, if any, have an effect on cell motility, and the degree to which motile cells are affected.

EXAMPLES

The invention is further described in the following examples, which do not limit the scope of the invention described in the claims.

Example 1—Device Modeling

To understand how a group of RBCs move through a baffle passageway, a 2-D finite-element model was employed using the COMSOL Multiphysics® software program, which performed biophysical modeling of chemoattractant diffusion in the device. The model was based on a strong solid-fluid coupling, which allows the incorporation of deformable solid bodies (e.g., RBCs) in fluid-filled channels. The channel geometries and initial RBC positions were inputted into a custom-built finite-element software package PAK45 and run on a desktop supercomputer consisting of 32 cores (Supermicro Super Server: 4×Eight-Core Intel Xeon Processor 2.70 GHz; 512 GB total memory). Using the model, the granular movement of RBCs through small channels was simulated. This movement is a result of the mutual interaction of many RBCs in the whole blood loading chamber, pushing the RBCs at the periphery to enter the connected microchannels. To simulate this force and induce movement, we assumed that the top-most RBC in the channel experiences an external force (equal to 1/(50 g), where g is gravitational acceleration constant. This was equivalent to a stack of twelve RBCs with 5% higher density than that of media pushing one RBC into the channels) in the y-direction. The other RBCs below the topmost RBC had no externally applied forces.

Figure 5A:
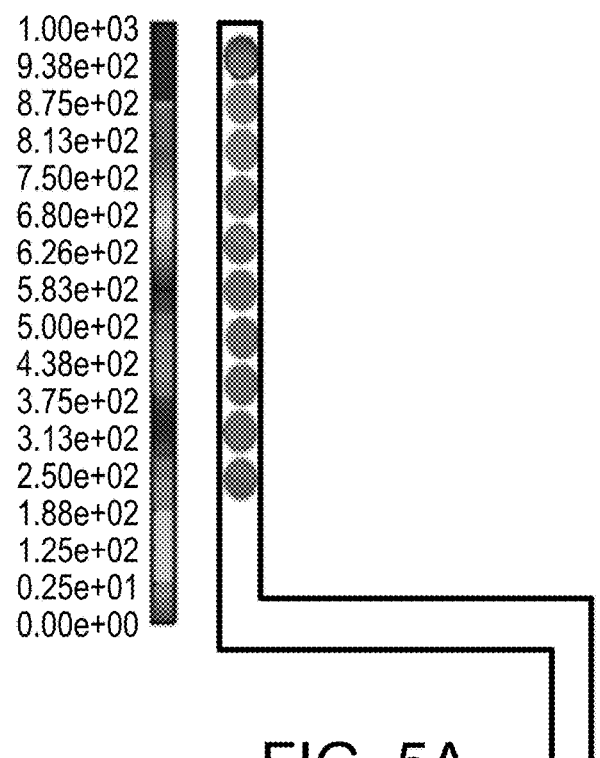
FIGS. 5A-5D are schematics depicting the different stages of red blood cells moving through a channel from an input chamber of a microfluidic device and subsequently traversing a 90° turn.
Figure 5B:
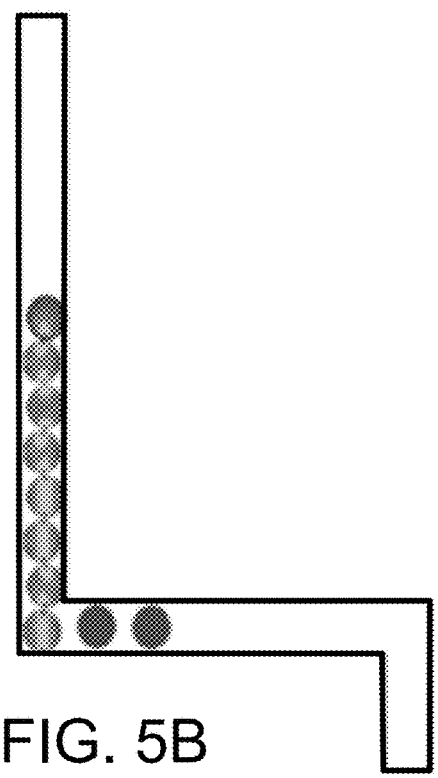
Figure 5C:
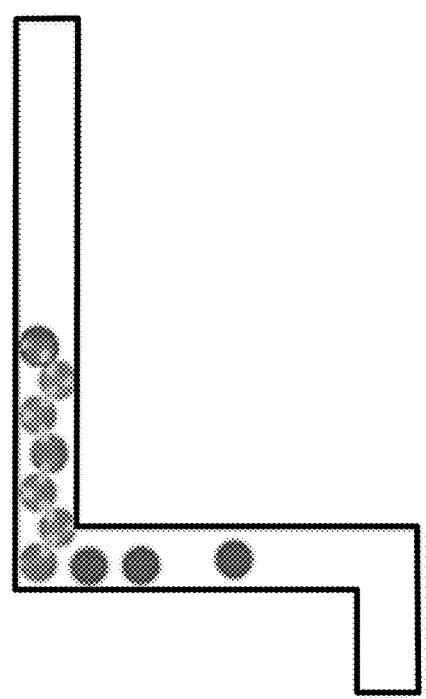
Figure 5D:
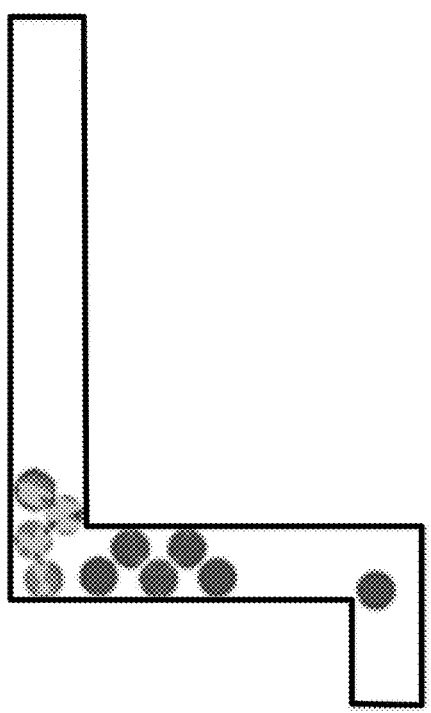

FIGS. 5A-5D are schematics depicting the different stages of RBCs moving through a channel from an input chamber and subsequently traversing a 90° turn. Three different passageway widths (9, 12, and 14 μm) were examined. Each RBC was assumed to have a diameter of 7.5 μm. FIG. 5A shows the initial RBC configuration of 10 RBCs in the entrance segment of a baffle passageway where the passageway width is 9 μm. The scale bar on the left of FIG. 5A is a color scale corresponding to different internal stresses that may be experienced by the RBCs during migration. FIG. 5B depicts the final steady-state configuration inside the 9 μm channel. FIG. 5B shows that as soon as one RBC is pushed into the corner, it substantially blocks the advance of all RBCs behind it by restricting the cross section of the passageway to less than one RBC diameter. Only two RBCs have moved pass the corner. This strategy is successful because the force pushing the RBCs is not enough to deform the cells through the corner of the passageway. FIG. 5C depicts the final steady-state configuration for a 12 μm channel after the same initial configuration shown in FIG. 5A. FIG. 5D depicts the final steady-state configuration for a 14 μm channel after the same initial configuration shown in FIG. 5A. The results in FIGS. 5C-5D demonstrate that reaching a stable configuration is less likely in larger channels when progressively more and more RBCs traverse the corner as the channel width increases.

Example 2—Comparison of Baffle to Straight Channel Design

To analyze the effectiveness of the baffle design containing restricted passageway cross-sections and turns for blocking RBCs versus that of a straight channel, one of each different device design was fabricated and tested with fMLP and LTB4 chemoattractants. The device containing the baffle was also analyzed for its ability to allow neutrophil migration.

Device Fabrication

Each microfluidic device was designed with three main components: chemokine side chambers (200×200 μm), a central whole-blood loading chamber, and migration channels that did or did not contain a RBC baffle region. The device containing the baffle included 10 short microfluidic channels (length~75 μm) connected horizontally through an approximately 200-μm-long channel to create several 90° bending sections capable of trapping the RBCs in order to prevent them from dispersing into the rest of the migration channel. All migration channels were designed to be 12 μm wide and 3 μm high.

The microfluidic devices were produced by replica molding polydimethylsiloxane (Sylgard 184, Elsworth Adhesives, Wilmington, Mass.) on a master wafer fabricated using standard photolithographic technologies with Mylar photomasks (FineLine Imaging, Colorado Springs, Colo.). After curing for at least 3 hours in an oven set to 65° C., the PDMS layer covering the master was peeled off and holes were punched. First, the central loading chamber was punched using a 1.5 mm puncher and then a 5 mm puncher was used to cut out the entire donut-shaped device (Harris Uni-Core, Ted Pella Inc., Reading, Ca). A 12-well plate was then plasma treated along with the PDMS donut-shaped devices and bonded on a hot plate set to 85° C. for 10 minutes.

Whole Blood Handling

Capillary blood (50 μL) was collected by pricking a finger of healthy volunteers. The blood was then pipetted into an eppendorf tube containing a mixed solution of HBSS media, heparin anti-coagulant (1.65 USP/50 μL of blood), and Hoescht stain (10 μL, 32.4 μM). The eppendorf tube was then incubated for 10 minutes at 37° C. and 5% $CO_2$ to allow for proper staining of the nuclei. Afterwards, 50 μL of the finger prick blood was pipetted into media containing the same Hoescht stain concentration as previously described and incubated for 10 minutes at 37° C. and 5% $CO_2$. Using a gel-loading tip, 2 uL of whole blood was slowly pipetted into the central input chamber of the device.

Establishing Chemoattractant Gradient

For the devices in which neutrophil migration was to be observed, the donut-shaped devices were filled with the chemoattractant solution of N-formyl-methionyl-leucyl-phenylalanine (fMLP) [100 nM] (Sigma-Aldrich, St. Louis, Mo.) or Leukotriene B4 (LTB4) (Caymen Chemicals, Ann Arbor, Mich.) [100 nM] immediately after the PDMS donut-shaped device was bonded to the well plate. The chemoattractant solution also contained fibronectin [25 nM] (Sigma-Aldrich, St. Louis, Mo.) to promote neutrophil surface adhesion. The chemoattractant was pipetted into the whole blood loading chamber (WBLC) and directly around the circumference of the device. The glass bottom 12-well plate was then placed in a desiccator to de-gas for 15 minutes to ensure proper filling of the chambers while the PDMS surface was still hydrophilic from plasma treatment. Afterwards, the central whole-blood loading chamber and the outside region surrounding the donut were washed thoroughly with Phosphate Buffered Saline (PBS) in each well to wash away excess chemoattractant. The wells of the plate were then filled with RPMI 1640 media and allowed to sit for a period of 15 minutes to generate stable chemoattractant gradients.

Results

Time-lapse imaging was performed on a Nikon Eclipse Ti microscope with 10-15× magnification and a biochamber heated to 37° C. with 5% $CO_2$ and 80% humidity. For each experiment in which an attractant gradient was established, at least 50 neutrophils were manually tracked.

Figure 6B:
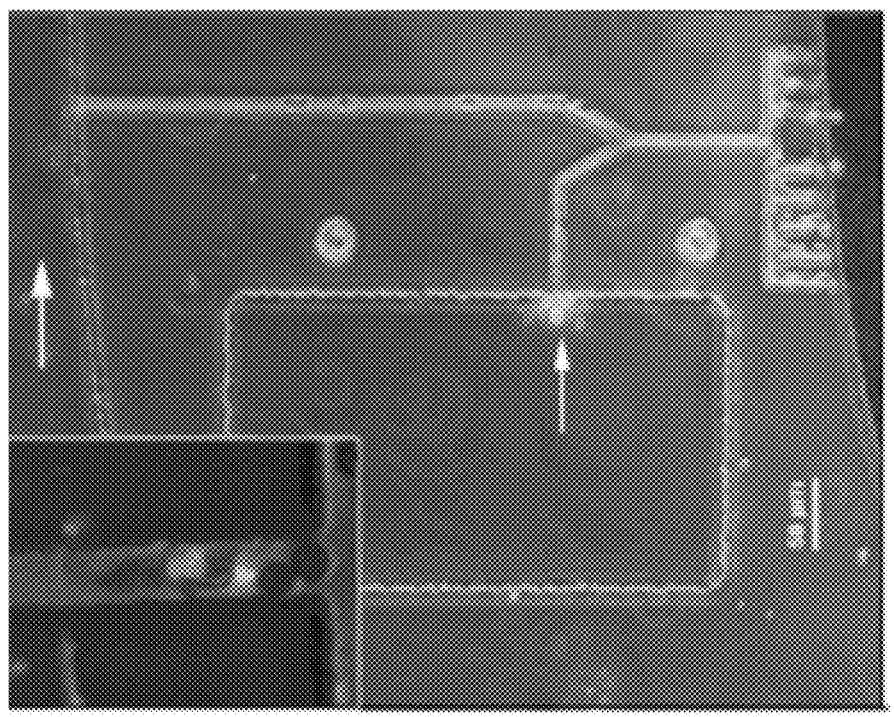
FIG. 6B is a BF image of a microfluidic device fabricated with a baffle to filter red blood cells.
Figure 6A:
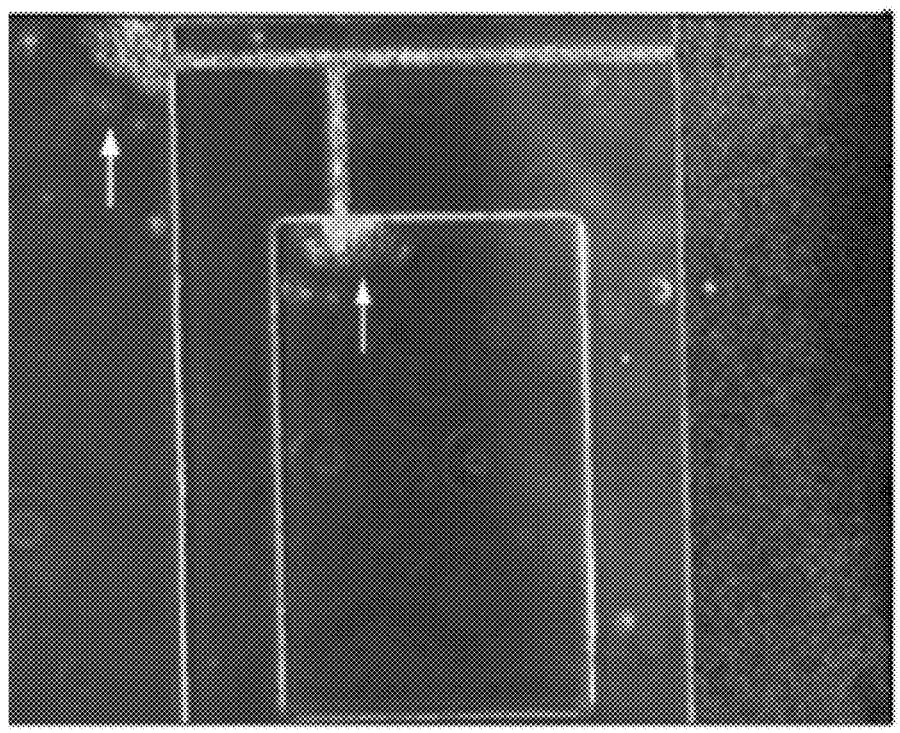
FIG. 6A is a bright-field (BF) image of a microfluidic device without a baffle to filter red blood cells.

FIG. 6A is a bright-field (BF) image of the device as fabricated above without a baffle to filter the RBCs. RBCs are seen to clog the migration channel and contaminate the attractant chamber (see arrows). FIG. 6B is a BF image of the device as fabricated above with a baffle to filter the RBCs. The incorporation of the RBC baffle upstream of the migration channel significantly reduces RBC contamination in the attractant chamber by 63% and eliminates RBCs at the channel exit. Thus, the baffle containing the comb design proved more efficient in blocking the entrance of RBCs in the migration channels compared to the straight channels.

FIGS. 7A-7H are time-lapse images of the device containing the comb-shaped baffle, where a LTB4 chemoattractant gradient was established between the attractant reservoir and the input chamber. As shown in FIGS. 7A-7H, few RBCs are able to enter the migration channel, while a neutrophil is able to migrate past the RBCs into the migration channel (see arrow in FIG. 7H). These results demonstrated that the microfluidic device is capable of inhibiting the movement of the RBCs relative to that of the neutrophils, without causing perturbations in cell motility or directionality. Integration of the on-chip baffle in the novel microfluidic device removes RBCs from actively migrating neutrophils and circumvents the need for cumbersome cell separation methods such as density gradients, positive selection, or negative selection, which are prone to introduce artifacts by activating neutrophils. The results also show that the microfluidic device produces a stable linear chemoattractant gradient without the need for peripherals like an outside pressure source (i.e. syringe pump).

Example 3—Assay Validation with Finger Prick and Venous Healthy Donor Blood Sources The microfluidic devices were also validated by loading whole blood from finger prick and venous sources, as well as isolated neutrophils toward the chemoattractant fMLP. Specifically, neutrophil migration was analyzed for whole blood from the finger prick, from the venous blood source, and from the isolated neutrophils. The devices were fabricated and the fMLP chemoattractant gradient was established as explained above in Example 2.

Whole Blood Handling

Capillary blood (50 µL) was collected by pricking a finger of healthy volunteers. The blood was then pipetted into an eppendorf tube containing a mixed solution of HBSS media, heparin anti-coagulant (1.65 USP/50 µL of blood), and Hoescht stain (10 µL, 32.4 µM). The eppendorf tube was then incubated for 10 minutes at 37° C. and 5% $CO_2$ to allow for proper staining of the nuclei. For venous blood samples, 10 mL of peripheral blood was drawn from a health volunteer into tubes containing 33 US Pherparin (Vacutainer, Becton Dickinson, Franklin Lakes, N.J.). Afterwards, 50 µL of the blood was pipetted into media containing the same Hoescht stain concentration as previously described and incubated for 10 minutes at 37° C. and 5% $CO_2$. Using a gel-loading tip, 2 uL of whole blood was slowly pipetted into the central input chamber of the device.

Neutrophil Isolation

To compare the whole blood results with neutrophil migration from an isolated sample, we also isolated human neutrophils from whole blood using HetaSep followed by the EasySep Human Neutrophil Enrichment Kits (STEMCELL Technologies Inc. Vancouver, Canada) following the manufacturer's protocol. The final aliquots of neutrophils were re-suspended in 1×HBSS+0.2% human serum albumin (Sigma-Aldrich, St. Louis, Mo.) at a density of ~40,000 cells/µL and kept at 37° C. cell until devices were properly primed.

Results

Time-lapse imaging was performed on a Nikon Eclipse Ti microscope with 10-15× magnification and a biochamber heated to 37° C. with 5% $CO_2$ and 80% humidity. For each experiment in which an attractant gradient was established, at least 50 neutrophils were manually tracked over a period of 200 min. Directionality of primed neutrophils was quantified by counting the number of cells that followed the chemotactic gradient and turned at the bifurcation toward the chemoattractant chamber as opposed to the number of cells that exited the device to the peripheral region. Cell velocities were calculated using Image J (NIH) and data analysis with GraphPad Prism.

Figure 8B:
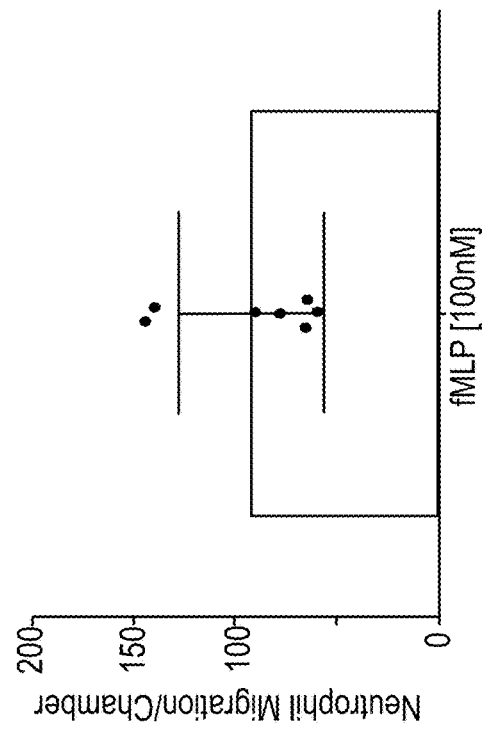
FIG. 8B is a plot of neutrophil migration counts per attractant chamber for whole blood samples obtained from seven different subjects.
Figure 8D:
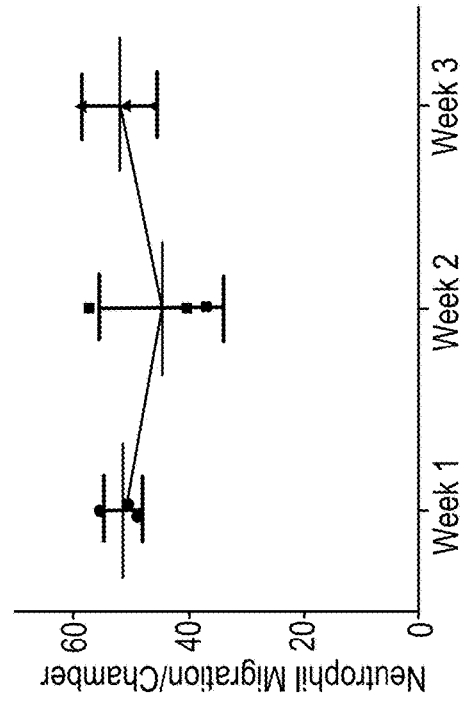
FIG. 8D is a plot of baseline neutrophil migration in a healthy subject over a three week time period.
Figure 8A:
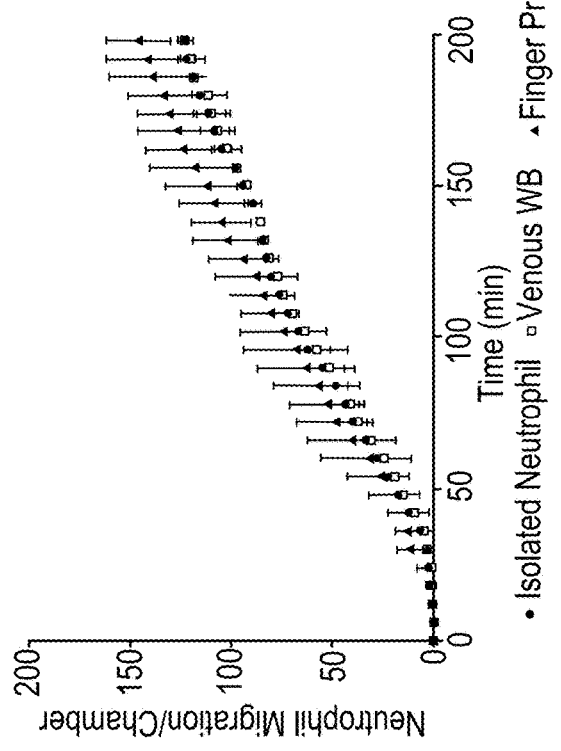
FIG. 8A is a plot of neutrophil migration counts for neutrophils from a venous blood source, a finger prick blood source, and for isolated neutrophils.

FIG. 8A is a plot of neutrophil migration counts among venous blood source, finger prick blood source, and isolated neutrophils. A similar delay time, accumulation rate and final cell count are observed in all three conditions migrating to fMLP [100 nM]. Graphs correspond to average cell counts (n=16) in all attractant chambers. Neutrophils from the two whole blood sources, as well as isolated neutrophils, began migrating towards the fMLP [100 nM] gradient within 20 minutes and neutrophil accumulation numbers from all three sources were consistent around 135±20 cells/device after 3.5 hours (P-value<0.001, $R^2$=0.98). The rate of neutrophil accumulation remained constant for the length of the 200 min experiment in all blood sources. As shown in FIG. 8A, we observed higher variability of neutrophil counts with the finger prick blood source compared to the venous or isolated neutrophil sources, which may reflect higher heterogeneity of the neutrophil population in the capillaries compared to the whole blood. These results suggest that the device will operate just as well as devices that require neutrophil isolation, but without the need to include the preliminary isolation step.

Figure 8C:
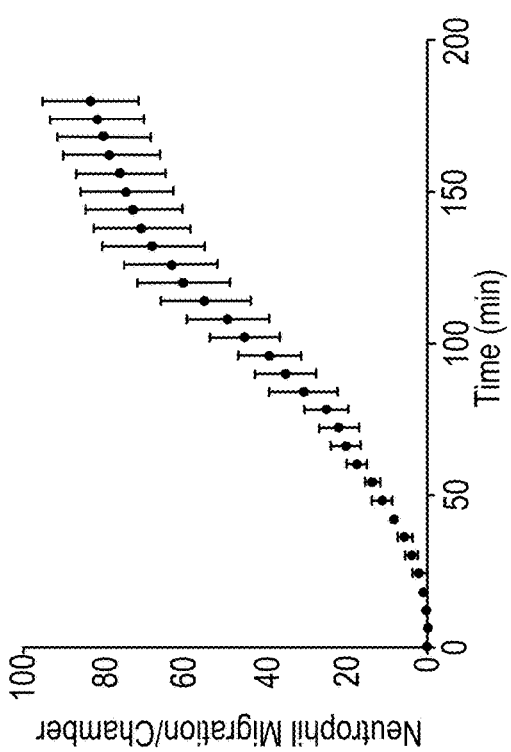
FIG. 8C is a plot of average neutrophil migration counts in six separate microfluidic devices.

We then measured variability between healthy donor neutrophil migration from whole blood finger source towards fMLP [100 nM]. FIG. 8B is a plot of neutrophil migration counts per chamber compared for the 7 healthy volunteers. Of interest, for 5 out of 7 donors' neutrophil migration counts clustered tightly around the average of 92±35 cells after 200 min. However, two donors had significantly higher neutrophil migration counts, which may be representative of the variation in innate To determine device-device variation, we loaded whole blood from a finger prick of a healthy donor into 6 separate devices and quantified neutrophil accumulation to a gradient of fMLP [100 nM]. FIG. 8C is a plot of the average neutrophil migration counts for the fMLP gradient in the 6 separate devices. The device-device variation was 14.1% (83±12 cells after 200 min.), over the duration of the experiment.

We also established a healthy donor baseline, measuring neutrophil accumulation from finger prick whole blood from the same healthy donor at one week intervals for a total of three weeks. FIG. 8D is a plot of the base-line for neutronphil migration in the healthy donor over the three week time period. The experiment yielded equivalent neutrophil accumulation values, thus suggesting high experimental reproducibility as well as a consistent accumulation baseline for the same volunteer. The confirmation of a consistent baseline of neutrophil recruitment in a healthy volunteer, suggests that perturbations in this baseline could represent significant clinical changes in the innate immune response, such as injury, infection or dysfunction that would be useful in diagnosis or predictions of future clinical outcomes.

Example 4—Neutrophil Chemotaxis Towards Standard Chemoattractants

Neutrophil migration toward different attractants (fMLP and LTB4) was also examined. The devices were fabricated and the fMLP and LTB4 chemoattractant gradients were established as explained above in Example 2. The concentrations of the three different chemoattractants were varied from 10 nM to 50 nM to 100 nM. Solutions containing fibronectin [25 nM] and exclusive of fibronection were prepared. Finger prick blood and venous blood were obtained as described above in Example 3. Velocity measurements were obtained as explained above in Example 3 using time-lapse imaging. Neutrophil migration toward the fMLP and the LTB4 chemoattractants were compared against a control device, in which no chemoattractant gradient was established.

Results

FIG. 9A is a plot of the dose-response of neutrophils migrating out of whole blood to the LTB4 and fMLP chemoattractants. The plots correspond to an average cell count reached in 16 different attractant chambers. As shown in FIG. 9A, the neutrophils do not migrate in the absence of a chemoattractant gradient. Overall, increased cells migration was observed at higher concentration. Maximal cell recruitment was observed at the 100 nM concentration in the attractant chamber of the microfluidic device. As shown in FIG. 9A, a gradient of fMLP [100 nM] recruited neutrophils from finger pick whole blood at a two-fold higher count (86±7 cells/device after 200 min) than LTB4 (39±12 cells/device after 200 min). FIG. 9B is a plot of neutrophil velocity from finger prick whole blood in response to fMLP and LTB4. As shown in FIG. 9B, neutrophil velocity was comparable for both fMLP (19±6 µm/min) and LTB4 (20±7 µm/min). Neutrophil velocities were also consistent between venous whole blood and finger prick whole blood for both fMLP and LTB4 chemoattractants.

The bifurcation in the microfluidic device design (i.e., where the exit channel splits off from the migration channel, see FIG. 1A) allows for the quantification of neutrophils directionality by comparing the number of cells that migrated towards the chemoattractant gradient to the number of cells that become "lost" and exit the device. This directional index is clinically relevant as it provides a quantitative measurement for correct neutrophil response to a site of injury or infection. The "lost" or non-directional neutrophils would potentially migrate and cause unnecessary damage to healthy tissue or organs. FIG. 9C is a plot that shows a directionality index for neutrophils in response to both fMLP and LTB4. Directionality is calculated by finding a ratio of the cells that correctly follow the attractant gradient to the attractant chamber divided by the total number of cells (cells that migrate to the attractant chamber plus the cells that exit the device). As shown in FIG. 9C, neutrophils from finger prick and venous healthy donor whole blood sources have a directionality index greater than 0.9 for both fMLP and LTB4.

The effect of fibronectin inclusion in the cheomattractant solution was also analyzed. Fibronectin promotes neutrophil adherence and acts as a blocking agent (in addition to 0.2% human serum albumin) for the glass surface of the device. FIG. 9D is a plot that shows neutrophil count in the fMLP attractant chamber for pin prick and venous blood in response to attractant with and without fibronection. As shown in FIG. 9D, fibronection does not appear to change final neutrophil counts migrating towards fMLP. The foregoing results demonstrate that the device is suitable for comparing motile cell response to different attractant gradients.

Example 5—Disfunction in Neutrophil Recruitment after Burn in Human Patient

We also utilized the novel microfluidic device to monitor neutrophil chemotaxis function in a burn patient.

Blood Samples

Blood samples of 1 mL were collected from one burn patient suffering from 24% total body surface area (TBSA) burn. Procedures for fabricating the device, preparing the chemoattractant gradient, and performing time-lapse imaging were conducted as explained above with respect to examples 2-4.

Results

Figures 10A, 10B, 10C:
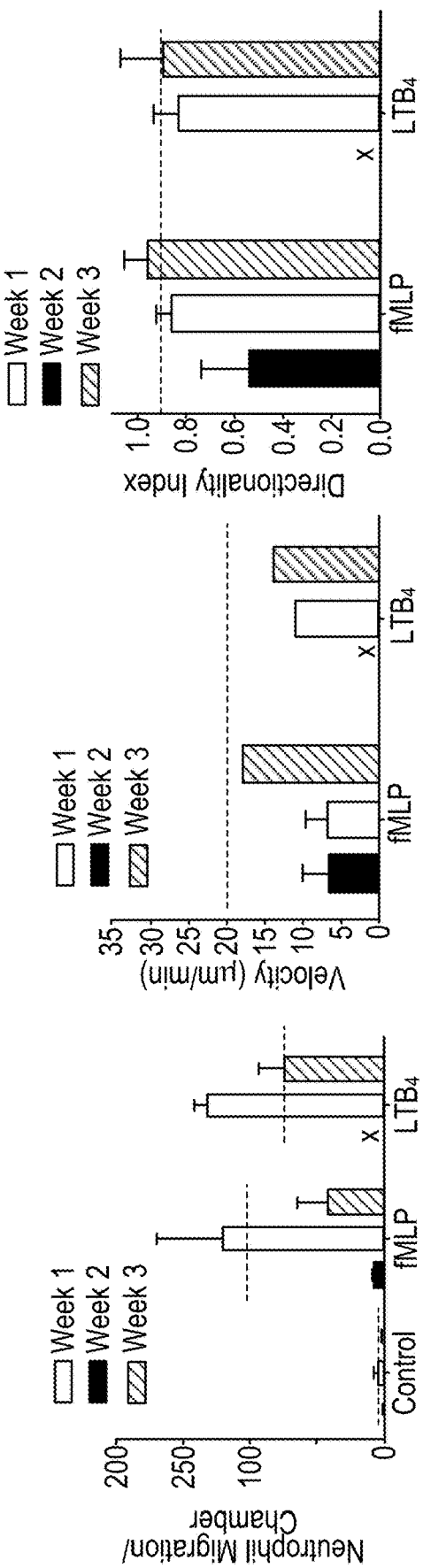
FIG. 10A is a plot of neutrophil migration counts in an attractant chamber with no chemoattractant gradient, with fMLP chemoattractant gradient, and with LTB4 chemoattractant gradient.
FIG. 10B is a plot of velocity of neutrophils migrating to LTB4 compared with fMLP over a three week period.
FIG. 10C is a plot of a directionality index of neutrophils migrating to LTB4 compared with fMLP.

Neutrophil chemotaxis was monitored over a 3 week treatment period. FIG. 10A is a plot of neutrophil migration counts in the attractant chamber with no chemoattractant gradient, with fMLP chemoattractant gradient [100 nM], and with LTB4 chemoattractant gradient [100 nM]. FIG. 10B is a plot of velocity [µm/min] of neutrophils migrating to LTB4 compared with fMLP over a three week period. FIG. 10C is a plot of directionality index of neutrophils migrating to LTB4 compared with fMLP. All graphs correspond to average cell counts across 16 attractant chambers.

As shown in FIG. 10A, there was an order of magnitude decrease in neutrophil cell count compared with the average range (shown with dotted line) of a healthy volunteer 1 week after the burn injury. Moreover, as shown in FIGS. 10B and 10C, we observed a 75% reduction in neutrophil velocity and a 50% reduction in directionality in neutrophils migrating toward a fMLP [100 nM] gradient. The number of cells accumulating towards fMLP spiked from below normal values to 15% above the normal healthy volunteer range at two weeks post burn, which corresponded to a period when the patient was observed to have a fever. At two weeks post-burn, neutrophil velocity remained impaired in both fMLP and LTB4 conditions (60% and 40% reduction respectively), but neutrophil directionality had been restored to the range of healthy volunteers. Three weeks post-burn, neutrophil cell counts to fMLP were lower than the average healthy volunteer count, whereas LTB4 accumulation counts were in the normal range. Velocity and directionality were both restored to the normal range 3 weeks post-burn. These results demonstrate the microfluidic device may be useful for monitoring variation in cell motility of subjects over prolonged periods.

Example 6—Comparison of Human, Rat and Murine Neutrophils

Animal models of human disease differ in innate immune responses to stress, pathogens, or injury. Current technologies for measuring neutrophil phenotype prevent precise inter-species comparisons because they require the separation of neutrophils from blood using species-specific protocols. For example, current neutrophil separation methods, developed originally for human donors, require large volumes of blood and are less suitable for mice due to their significantly lower circulatory volume. Therefore, many studies on mouse neutrophils are done with bone marrow cells. However, bone marrow neutrophils appear to be heterogeneous and functionally immature. Furthermore, standard negative enrichment of neutrophils include a lengthy (3 hour) protocols during which the neutrophil phenotype can change. Moreover, antibody cocktails for neutrophil isolation are less specific for mouse than human and activation levels of neutrophils affect the purity and yield. However, by using the novel microfluidic device described herein, we performed a robust characterization of neutrophil migratory phenotypes from different species directly from a droplet of whole blood. In particular, using the new device, neutrophil measurements were performed from minute volumes (less than 2 µL) of whole blood (WB), from various species donors (rat, murine and human), with high precision and single cell resolution.

Microfluidic Device Fabrication

The microfluidic device to study mouse, rat and human neutrophil chemotaxis from one droplet of whole blood was designed with three main components: focal chemoattractant chambers (FCCs) (200×200 µm), a central whole-blood loading chamber, and migration channels containing RBC filtering regions. The filter for each migration channel included 10 short channels (Length~75 µm) with a 3.5 µm narrowing region ('pinch') connected horizontally through an approximately 200-µm-long channel to create 90° bending sections capable of trapping the RBCs to prevent them from dispersing into the rest of the migration channel. All migration channels were designed to be 12 µm wide and 3 µm high to establish only a single column of RBCs for efficient trapping while allowing active mouse, rat and human neutrophils to easily migrate through. The devices were fabricated as described above in Example 2.

Whole Blood Sample Collection

For humans, 50 µL of capillary blood was collected by pricking a finger of healthy volunteers. For mice, 50 µL of capillary blood was collected by the facial vein method (Institutional animal care and use Protocol #2007N000136) requiring no anesthesia. For rats, 50 µL of venous blood was collected from the tail vein (Institutional animal care and use Protocol #2012N000034) using 1-2% Isoflurane inhalant. The blood was then pipetted into an eppendorf tube containing a mixed solution of HBSS media, heparin anticoagulant (1.65 USP/50 µL of blood), and Hoechst stain (10 µL, 32.4 µM). The eppendorf tube was then incubated for 10 minutes at 37° C. and 5% $CO_2$ to allow for proper staining of the nuclei.

Device Priming and Cell Loading

All reagents and whole blood were pipetted into the device and there was no flow or requirement of external syringe pump. A gradient of the chemoattractant was established along the migration channels by diffusion between the chemoattractant chambers and the central loading chamber. Prior to cell loading and immediately after bonding to the well plate, donut-shaped devices were filled with the chemoattractant solution containing 25 nM of fibronectin (Sigma-Aldrich, St. Louis, Mo.). The well plate was then placed in a desiccator under vacuum to de-gas for 15 minutes to ensure proper filling of the chambers while the PDMS surface was still hydrophilic. Afterwards, the central whole-blood loading chamber and the outside region surrounding the donut were washed thoroughly in each well to establish the gradient along the migration channels. The wells of the plate were then filled with RPMI 1640 media and allowed to sit for a period of 15 minutes to generate stable chemoattractant gradients. Finally, using a gel-lading tip, 2 µL of whole blood was slowly pipetted into the central whole-blood loading chamber.

Chemotaxis Imaging and Measurements

Time-lapse imaging was performed on a Nikon Eclipse Ti microscope with 10-15× magnification and a biochamber heated to 37° C. with 5% $CO_2$ and 80% humidity. Separate experiments to characterize the formation of gradients along the migration channels in the absence of cells were performed under similar temperature and gas conditions but by replacing the chemoattractant with fluorescein (Sigma-Aldrich, St. Louis, Mo.) of molecular weight comparable to that of fMLP (MW=438) and LTB4 (MW=336). For each experiment, at least 50 neutrophils were manually tracked. Directionality of primed neutrophils was quantified by counting the number of cells that followed the chemotactic gradient and turned at the bifurcation toward the chemoattractant chamber as opposed to the number of cells that exited the device to the peripheral region. Cell velocities were calculated using ImageJ (NIH). Total percentage of neutrophils to migrate was estimated using a COMSOL simulation model that estimated that 30.6% of area in whole blood loading chamber from which neutrophils could migrate in experimental time to be above critical gradient concentration. For an average human experiment, this would estimate~277 neutrophils per well that are exposed to chemoattractant gradient.

Results

An important feature that enabled the use of WB directly in the microfluidic device was the red blood cell (RBC) filter. Murine RBCs (average diameter=6 µm, thickness=1 µm) are of smaller geometry than human (average diameter=7-8 µm, thickness=2 µm). The RBC filter combined flat channels, a comb of 90° angles, and a 3.5 µm 'pinch' of square cross section to prevent the granular-flow of RBCs into the neutrophil migration channels. RBCs pushing on each other under the effect of gravity, were mechanically blocked at the entrance of the channels and remained confined inside the central loading chamber. The neutrophil migration channels remain clear because the blocked RBCs do not clog the channel and sufficient space remains between the RBC membrane and the channels walls to allow chemokine diffusion. Thus, the formation of neutrophil-guiding gradients from the WB to the FCC, along the migration channel, was unperturbed. Neutrophils were able to actively deform and migrate through the pinch, which assured the selectivity of the assay by preventing the migration of lymphocytes and monocytes, which deform less and require larger channels for migration. The selectivity was verified by observing the characteristic polymorph shape of the nucleus of moving cells. Once the neutrophils passed the pinch, they continued to follow the chemoattractant gradient along the migration channel and enter the FCC. The bifurcation in the channel created a 'decision point' where neutrophils can migrate toward or away from the chemoattractant gradient, providing critical information about their directionality.

To compare neutrophil migration phenotype between species, we measured chemotaxis to two standard chemoattractants (fMLP and LTB4) in humans, C57BL/6 and Sv129S6 mice and Wistar rats. Human neutrophils in 2 μL whole blood samples migrated towards fMLP (55.8±19.8%) and LTB4 (54.0±5.6%) (see FIG. 11A). A lower percentage of Wistar rat neutrophils migrated to fMLP and LTB4 (10.9±8.5 and 2.8±1.1%, respectively). Surprisingly, LTB4 was the only chemoattractant able to induce significant neutrophil migration in all mouse neutrophils tested: Sv129S6 (99.5±13%) and C57BL/6 (52.7±24%). The velocity of C57BL/6 neutrophils towards fMLP (13±7.4 μm/min) was ~2.5-fold lower than that of Sv129S6 (19.7±8.7 μm/min), rat (26.2±5.9 μm/min), or human (23.4±5.4 μm/min) neutrophils (see FIG. 11B). The directional index of C57BL/6 neutrophils toward fMLP (0.61±0.07) was comparable to that of rat neutrophils (0.62±0.12) and significantly lower than that of Sv129S6 (0.82±0.06) or human (0.85±0.06) neutrophils (see FIG. 11C). The velocity and directionality deficits in C57BL/6 neutrophils have multiplicative effects and suggest less effective neutrophil migration upon stimulation.

The directionality of Sv129S6 mouse neutrophils towards C5a was lower than in humans, while directionality towards LTB4 was comparable (FIGS. 12C-D). C5a activation of mouse neutrophils led to random migration. These patterns of neutrophil migration in response to C5a are consistent with migration patterns reported previously from isolated human neutrophils. More human neutrophils migrated in response to C5a in the FCC than mouse neutrophils (26.8±5.9% versus 1±0.8%, FIG. 12A), and more neutrophils were activated by C5a compared to Sv129S6 mouse neutrophils (63.3±7.6% versus 18.3±3%, FIG. 12B).

The results demonstrate fundamental differences in neutrophil migratory responses between mice, rats and humans. Amongst hundreds of laboratory mouse strains available, two-thirds of all murine research is undertaken with the C57BL/6J (B6) strain (compared to 1% for Sv129S6) because of its robustness and availability of congenic strains. As therapies for human diseases become specifically targeted, it is increasingly important to further understand mouse strain differences in innate immune function and to wisely choose a mouse strain that most accurately models the human response to disease or drug therapeutic interventions. Using the new microfluidic device described herein, our results show that strain differences in neutrophil migratory function between common laboratory mouse models are significant and must be considered when selecting the appropriate model to mimic human infection or inflammation.

The novel device and techniques described herein were used to allow precise measurement of neutrophil chemotaxis from micro-volume samples of murine, rat and human blood in the same conditions and following the same sample preparation protocols. The assay was performed in the presence of all blood components, and was highly multiplexed. The results demonstrate that the novel device and techniques may be used by researchers to understand species and mouse strain differences in neutrophil migratory phenotypes from conscious animals over time. Compared to traditional methods (ie.g., transwell assay), the device avoids lengthy neutrophil isolation steps, uses micro-volume amounts of blood from conscious animals, which allows for repeated measures without potential confounding effects of anesthetic drugs, and provides single-cell-resolution information regarding neutrophil directionality and speed. The novel microfluidic device and techniques described herein also have two specific advantages compared to recent techniques that rely on neutrophil capture from blood by selective adhesion e.g. P-selectin. First, by avoiding the cell washing steps, the new device preserves the integrity of the blood sample, and with it important cues that may modulate neutrophil activity from serum or other cells in the whole blood. Second, by relying on physical (channel geometry) rather than biological mechanisms (selectins or endothelial cells) to achieve selectivity for neutrophils, the device eliminates the artificial activation of neutrophils via capture mechanisms and the need for species-matched capture molecules. The requirement of small numbers of cells is particularly advantageous when studying mice, where blood volumes are limited. The novel device and techniques described herein also eliminate the necessity of pooling blood from several animals and permits repeated single animal neutrophil phenotype data measurements over-time, so as to potentially monitor progression of disease and/or therapeutic responses. Measuring neutrophil migration in the whole blood native microenvironment mimics the in vivo, holistic animal response more accurately.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A device comprising:
an input chamber;
an attractant chamber;
a migration channel arranged in fluid communication between an outlet of the input chamber and an inlet of the attractant chamber;
a comb-shaped baffle arranged in fluid communication between the outlet of the input chamber and the migration channel or within the migration channel,
wherein the comb-shaped baffle comprises a first fluid passage in fluid communication with a second fluid passage,
wherein an angle between a sample transport path in the first fluid passage and a sample transport path the second fluid passage is greater than or equal to about 45 degrees,
wherein the baffle is configured to inhibit movement of a first type of cell through the baffle to a greater extent than the baffle inhibits movement of a second type of cell through the baffle; and an exit channel in fluid communication with the migration channel at a point beyond the baffle and before the migration channel enters the inlet of the attractant chamber.

2. The device of claim 1, wherein the angle is about 90 degrees.

3. The device of claim 1, wherein a cross-sectional area of the first fluid passage normal to the sample transport path in the first fluid passage is greater than a cross-sectional area of the first type of cell, and wherein a height of the cross-sectional area is greater than a thickness of the first type of cell and less than a diameter of the first type of cell, and a width of the cross-sectional area is greater than the diameter of the first type of cell.

4. The device of claim 3, wherein the height of the cross-sectional area is greater than about 2 microns and less than about 6 microns, and wherein the width of the cross-sectional area is greater than about 6 microns.

5. The device of claim 1, wherein a volume of the input chamber is greater than about 1 microliter and less than about 5 microliters.

6. The device of claim 1, wherein a length of a fluid transport path through the migration channel is between about 10 microns and about 2000 microns.

7. The device of claim 1, wherein the baffle comprises:
a plurality of first fluid passages; and
a plurality of second fluid passages, each first fluid passage being in fluid communication with the outlet of the input chamber and in fluid communication with a corresponding second fluid passage,
wherein an angle between a fluid transport path of each first fluid passage and a sample transport path of the corresponding second fluid passage is greater than or equal to about 45 degrees.

8. The device of claim 7, wherein the plurality of first fluid passages are arranged in parallel.

9. The device of claim 7, wherein the angle between a first fluid transport path and a first sample transport path is different from the angle between a second fluid transport path and a second sample transport path.

10. The device of claim 1, wherein the input chamber, the migration channel, or both the input chamber and the migration channel are coated with a protein.

11. The device of claim 10, wherein the protein is configured to prevent neutrophil adhesion.

12. The device of claim 10, wherein the protein is albumin.

13. The device of claim 10, wherein the protein is configured to promote neutrophil activation.

14. The device of claim 10, wherein the protein is P selectin.

15. The device of claim 1, wherein the first type of cell is a red blood cell or a leukocyte, and the second type of cell is a neutrophil.

16. A system comprising:
a device comprising an input chamber,
an attractant chamber,
a migration channel arranged in fluid communication between an outlet of the input chamber and inlet of the attractant chamber,
a comb-shaped baffle arranged in fluid communication between the outlet of the input chamber and the migration channel or within the migration channel,
wherein the baffle comprises a first fluid passage in fluid communication with a second fluid passage,
wherein an angle between a sample transport path in the first fluid passage and a sample transport path the second fluid passage is greater than or equal to about 45 degrees,
wherein the baffle is configured to inhibit movement of a first type of cell through the baffle to a greater extent than the baffle inhibits movement of a second type of cell through the baffle, and
an exit channel in fluid communication with the migration channel at a point beyond the baffle and before the migration channel enters the inlet of the attractant chamber; and
a control apparatus configured to image a number of cells migrating from the input chamber through the baffle and the migration channel to the attractant chamber.

17. The system of claim 16, wherein a cross-sectional area of the first fluid passage normal to the sample transport path in the first fluid passage is greater than a cross-sectional area of the first type of cell, and
wherein a height of the cross-sectional area is greater than a thickness of the first type of cell and less than a diameter of the first type of cell, and a width of the cross-sectional area is greater than the diameter of the first type of cell.

18. The system of claim 16, wherein the baffle comprises:
a plurality of first fluid passages; and
a plurality of second fluid passages, each first fluid passage being in fluid communication with the outlet of the input chamber and in fluid communication with a corresponding second fluid passage,
wherein an angle between a fluid transport path of each first fluid passage and a sample transport path of the corresponding second fluid passage is greater than or equal to about 45 degrees.

* * * * *

UNITED STATES PATENT AND TRADEMARK OFFICE
CERTIFICATE OF CORRECTION

PATENT NO. : 11,460,465 B2
APPLICATION NO. : 16/885760
DATED : October 4, 2022
INVENTOR(S) : Daniel Irimia, Caroline Jones and Anh Hoang It is certified that error appears in the above-identified patent and that said Letters Patent is hereby corrected as shown below:

In the Claims

Column 26, Line 61:
In Claim 1, after "path" insert -- in --

Column 28, Line 17 (approx.):
In Claim 16, after "path" insert -- in --

Signed and Sealed this
Twentieth Day of December, 2022

Katherine Kelly Vidal
*Director of the United States Patent and Trademark Office*